(12) United States Patent
Lachia et al.

(10) Patent No.: US 10,399,950 B2
(45) Date of Patent: Sep. 3, 2019

(54) SUBSTITUTED AMINO AZOLES AS PLANT GROWTH REGULATORS

(71) Applicants: SYNGENTA PARTICIPATIONS AG, Basel (CH); SYNGENTA LIMITED, Surrey (GB)

(72) Inventors: Mathilde Denise Lachia, Stein (CH); Pierre Joseph Marcel Jung, Stein (CH); Joerg Leipner, Stein (CH); David Brocklehurst, Berkshire (GB); Alain De Mesmaeker, Stein (CH); Sebastian Volker Wendeborn, Stein (CH)

(73) Assignee: Syngenta Partcipations AG, Basel (CH)

( * ) Notice: Subject to any disclaimer, the term of this patent is extended or adjusted under 35 U.S.C. 154(b) by 53 days.

(21) Appl. No.: 14/765,359

(22) PCT Filed: Jan. 31, 2014

(86) PCT No.: PCT/EP2014/051872
§ 371 (c)(1),
(2) Date: Aug. 3, 2015

(87) PCT Pub. No.: WO2014/122066
PCT Pub. Date: Aug. 14, 2014

(65) Prior Publication Data
US 2015/0376150 A1    Dec. 31, 2015

(30) Foreign Application Priority Data
Feb. 5, 2013 (EP) .................................... 13154005

(51) Int. Cl.
| | | |
|---|---|---|
| *A01N 43/78* | (2006.01) | |
| *A01N 47/40* | (2006.01) | |
| *C07D 277/46* | (2006.01) | |
| *C07D 417/04* | (2006.01) | |
| *C07D 277/56* | (2006.01) | |

(52) U.S. Cl.
CPC .......... *C07D 277/46* (2013.01); *A01N 43/78* (2013.01); *A01N 47/40* (2013.01); *C07D 277/56* (2013.01); *C07D 417/04* (2013.01)

(58) Field of Classification Search
None
See application file for complete search history.

(56) References Cited

U.S. PATENT DOCUMENTS 7,037,929 B1 *  5/2006  Pevarello .............. A61K 31/426
                                                   514/235.5
8,404,684 B2 *  3/2013  Bruce ................... C07D 417/04
                                                   514/235.8

FOREIGN PATENT DOCUMENTS

| EP | 0566138 A1 | 4/1993 | |
|---|---|---|---|
| EP | 0566138 A1 * | 10/1993 | .............. A01N 43/78 |
| WO | WO-0026202 A1 * | 5/2000 | ............ A61K 31/426 |
| WO | 2004/096797 A1 | 11/2004 | |
| WO | WO-2004096797 A1 * | 11/2004 | ............ C07D 417/04 |
| WO | 2008/049729 A1 | 5/2008 | |
| WO | 2009/109570 A1 | 9/2009 | |

OTHER PUBLICATIONS

Werbel et al.(Derivatives of 2-amino-5-nitrothiazole as potential schistosmicides, J. Med. Chem., 1971, vol. 14 issue 1, pp. 10-16.*
Islip et al.(Antiparasitic 5-nitrothiazoles and 5-nitro-4-thiazolines, J. Med. Chem. 1973, vol. 16 No. 9, pp. 1027-1030).*
Werbel et al.(Derivatives of 2-amino-5-nitrothiazole as potential schistosmicides, J. Med. Chem., 1971, vol. 14 issue 1, pp. 10-16). (Year: 1971).*
Islip et al.(Antiparasitic 5-nitrothiazoles and 5-nitro-4-thiazolines, J. Med. Chem. 1973, vol. 16 No. 9, pp. 1027-1030) (Year: 1973).*
Garreau (Amides of halogenated aminothiazoles, Compt. Rend., 1956, 242, 1036-8) (Year: 1956).*
Peter J. Islip, et al., "Antiparasitic 5-Nitrothiazoles and 5-Nitro-4-thiazolines", Journal of Medicinal Chemistry, (1973), vol. 16, No. 9.
"Nitrite substitutes for controlling Clostridium botulinum", XP-002698483 Retrieved from CAPLUS Database accession No. 1986-87265 abstract & Developments in Industrial Microbiology Series, vol. 25, pp. 349-362 Jan. 1, 1984.
International Search Report for International Patent Application No. PCT/EP2014/051872 dated Apr. 3, 2014.

* cited by examiner

*Primary Examiner* — Alton N Pryor
(74) *Attorney, Agent, or Firm* — Baker & Hostetler LLP; Toni-Junell Herbert

(57) ABSTRACT

The present invention relates to novel non-steroidal brassinosteroid mimetic derivatives of formula (I) as defined herein, to processes and intermediates for preparing them, to plant growth regulator compositions comprising them and to methods of using them for controlling the growth of plants and/or promoting the germination of seeds.

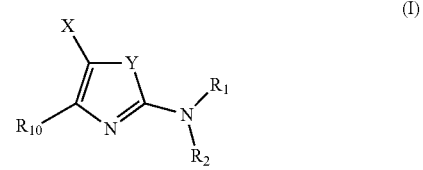

16 Claims, No Drawings

SUBSTITUTED AMINO AZOLES AS PLANT GROWTH REGULATORS

This application is a 371 filing of International Application No. PCT/EP2014/051872, filed Jan. 31, 2014, which claims priority benefit to EP Patent Application No. 13154005.6 filed Feb. 5, 2013, the contents of all of which are incorporated herein by reference.

The present invention relates to novel non-steroidal brassinosteroid mimetic derivatives, to processes and intermediates for preparing them, to plant growth regulator compositions comprising them and to methods of using them for controlling the growth of plants and/or promoting the germination of seeds.

EP0566138 describes aminothiazole derivatives and their use as fungicides. WO 2004/096797 describes aminothiazole derivatives that have a pharmaceutical action in inhibiting phosphatidylinositol 3-kinase.

Various chemical derivatives that act on the brassinosteroid signalling pathway have been described, for example, in *Bioorg. Med. Chem.* 1998, 6:1975; *Bioorg. Med. Chem. Let.* 1999, 9:425; *J. Agric. Food Chem.* 2002, 50:3486; *Planta* 2001, 213:716; WO2008/049729, WO2009/109570 and Chemistry & Biology 2009, 16:594-604. Brassinosteroids and analogues thereof have been described to have useful plant growth regulating properties.

It has now surprisingly been found that certain new non-steroidal brassinosteroid mimetic derivatives have properties that are useful for controlling the growth of plants and/or promoting the germination of seeds. Preferably, the new compounds may result in improved plant growth properties, such as faster growth, faster germination, earlier germination, and/or reduced toxicity. The compounds may offer other advantages such as enhanced solubility, or be more advantageously formulated, provide more efficient delivery to the plant, provide improved uptake into the plant, or be more readily biodegradable.

According to the present invention, there is provided a compound of formula (I)

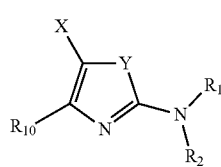

wherein, Y is O or S;
$R_{10}$ is H, halogen, $C_1$-$C_6$ alkyl, $C_1$-$C_6$ alkoxy, $C_1$-$C_6$ haloalkyl or cyano, X is halogen, $C_1$-$C_6$ haloalkyl, cyano, thiocyanate, nitro, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_2$-$C_6$ alkenyl, $C_2$-$C_6$ alkynyl, amine, N—$C_1$-$C_6$ alkyl amine, N,N-di-$C_1$-$C_6$ alkyl amine, $C_1$-$C_6$ alkylcarbonyl, $C_1$-$C_6$ alkoxycarbonyl, $C_1$-$C_6$ haloalkoxycarbonyl, $C_1$-$C_6$ haloalkylcarbonyl, $C_3$-$C_8$ cycloalkyl, formyl or mercapto; or X is heteroaryl or heteroaryl substituted by one or more halogen, cyano, $C_1$-$C_3$ alkyl, $C_1$-$C_3$ haloalkyl;
$R_1$ is H, $C_1$-$C_6$ alkyl, $C_1$-$C_6$ haloalkyl, $C_1$-$C_6$ alkylcarbonyl, $C_1$-$C_6$ alkoxycarbonyl; or $R_1$ is $C_1$-$C_6$ alkyl substituted by one or more cyano, amine, carbonylamine;

$R_2$ is a group according to formula (I')

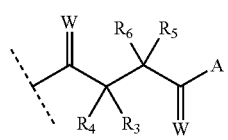

or $R_1$ and $R_2$ form a cyclic group around the nitrogen of formula (I")

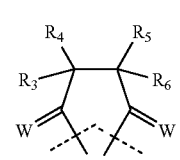

wherein each W is independently O or S;
A is —$OR_7$ or —NHCN;
$R_3$, $R_4$, $R_5$ and $R_6$ and are independently hydrogen, halogen, nitro, cyano, $C_1$-$C_3$ alkyl, $C_1$-$C_3$ haloalkyl, $C_1$-$C_3$ alkoxy, hydroxyl, —OC(O)$R_8$, amine, N—$C_1$-$C_3$ alkyl amine or N,N-di-$C_1$-$C_3$ alkyl amine;
$R_8$ is hydrogen, $C_1$-$C_6$ alkyl, $C_1$-$C_6$ alkoxy, or $C_1$-$C_6$ haloalkyl;
$R_7$ is hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, aryl or aryl substituted by one to five substituents $R_9$, heterocyclyl or heterocyclyl substituted by one to five substituents $R_9$;
or $R_7$ is $C_1$-$C_6$ alkyl substituted by one or more cyano, nitro, amine, hydroxyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkyl-sulfinyl, $C_1$-$C_6$ alkylsulfonyl, $C_1$-$C_6$ haloalkylsulfonyl, $C_3$-$C_7$ cycloalkyl, N—$C_1$-$C_6$ alkyl amine, N,N-di-$C_1$-$C_6$ alkyl amine, aryl or aryl substituted by one to five substituents $R_9$, heterocyclyl or heterocyclyl substituted by one to five substituents $R_9$;
each $R_9$ is independently cyano, nitro, amino, hydroxyl, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, N—$C_1$-$C_6$ alkyl-amino, N,N-di-($C_1$-$C_6$ alkyl)amino, N,N-di-($C_1$-$C_6$ alkyl)aminocarbonyl, N,N-di-($C_1$-$C_6$ alkyl)-aminosulfonyl, $C_1$-$C_6$ alkylcarbonyl, $C_1$-$C_6$ alkylcarbonyloxy, $C_1$-$C_6$ alkoxycarbonyl, $C_1$-$C_6$ alkyl-carbonylamino;
and any salts or N-oxides thereof;
excluding the following compounds according to formulae (i) to (viii):

i)

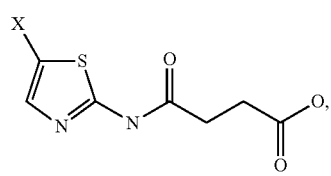

wherein X is NO$_2$, HC(O) or Br;

ii)

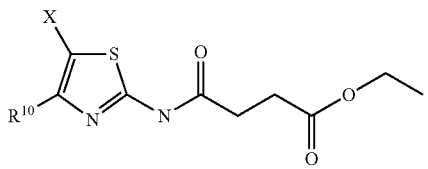

wherein X is CN or Br and R$_{10}$ is H; or wherein X is CN and R$_{10}$ is CF$_3$;

iii)

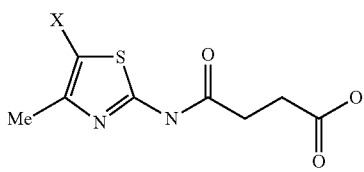

wherein X is Br, I, COCH$_2$Br, C(O)Me, COOMe, COOEt, COO$^i$Pr or COO$^i$Bu;

iv)

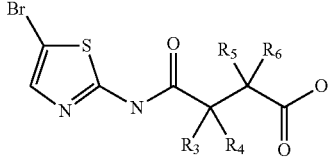

wherein R$_3$ is H and R$_4$ is NH$_2$ and R$_5$, R$_6$ are H; or wherein R$_3$, R$_4$ are H and R$_5$, R$_6$ are ethyl; or wherein R$_3$, R$_4$ are H and R$_5$ is methyl and R$_6$ is $^i$Pr;

v)

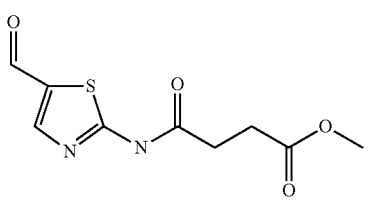

vi)

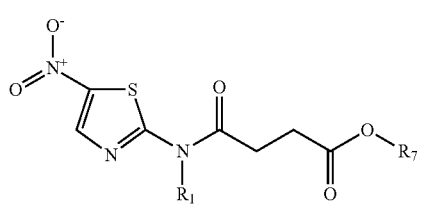

wherein R$_1$ is CH$_2$CH$_2$CONH$_2$ or CH$_2$CH$_2$CN and R$_7$ is methyl or ethyl;

vii)

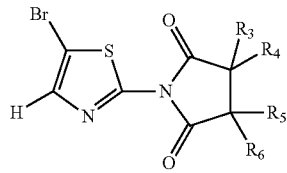

wherein R$_3$, R$_4$, R$_5$, R$_6$ are H; or wherein R$_3$, R$_4$ are H and R$_5$, R$_6$ are ethyl; or wherein R$_3$, R$_4$ are H and R$_5$ is methyl and R$_6$ is $^i$Pr; or wherein R$_3$ is methyl and R$_4$, R$_5$, R$_6$ are H;

viii)

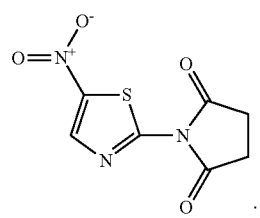

The compounds of formula (I) may exist in different geometric or optical isomers (diastereoisomers and enantiomers) or tautomeric forms. This invention covers all such isomers and tautomers and mixtures thereof in all proportions as well as isotopic forms such as deuterated compounds. The invention also covers all salts, N-oxides, and metalloidic complexes of the compounds of formula (I), including those of formula (i) to (viii).

Each alkyl moiety either alone or as part of a larger group (such as alkoxy, alkoxy-carbonyl, alkylcarbonyl, alkylaminocarbonyl, dialkylaminocarbonyl) is a straight or branched chain and is, for example, methyl, ethyl, n-propyl, n-butyl, n-pentyl, n-hexyl, iso-propyl, n-butyl, sec-butyl, iso-butyl, tert-butyl or neo-pentyl. The alkyl groups are preferably C$_1$-C$_6$ alkyl groups, more preferably C$_1$-C$_4$ and most preferably C$_1$-C$_3$ alkyl groups.

Each Alkenyl moiety either alone or as part of a larger group (such as alkoxy, alkoxy-carbonyl, alkylcarbonyl, alkylaminocarbonyl, dialkylaminocarbonyl) is having at least one carbon-carbon double bond and is, for example, vinyl, allyl. The alkenyl groups are preferably C$_2$-C$_6$ alkenyl groups, more preferably C$_2$-C$_4$ alkenyl groups.

Each alkynyl moiety either alone or as part of a larger group (such as alkoxy, alkoxy-carbonyl, alkylcarbonyl, alkylaminocarbonyl, dialkylaminocarbonyl) is having at least one carbon-carbon triple bond and is, for example, ethynyl, propargyl. The alkynyl groups are preferably C$_2$-C$_6$ alkynyl groups, more preferably C$_2$-C$_4$ alkynyl groups. The term "alkynyl", as used herein, unless otherwise indicated, includes alkyl moieties having at least one carbon-carbon triple bond wherein alkyl is as defined above.

Halogen is fluorine, chlorine, bromine or iodine.

Haloalkyl groups (either alone or as part of a larger group, such as haloalkoxy or haloalkylthio) are alkyl groups which are substituted with one or more of the same or different halogen atoms and are, for example, —CF$_3$, —CF$_2$Cl, —CH$_2$CF$_3$ or —CH$_2$CHF$_2$.

Hydroxyalkyl groups are alkyl groups which are substituted with one or more hydroxyl group and are, for example, —CH$_2$OH, —CH$_2$CH$_2$OH or —CH(OH)CH$_3$.

Alkoxy group are alkyl groups which are link with one or more oxygen atom and are, for example, —OCH$_3$, —OCH$_2$CH$_3$, —OCH(CH$_3$)CH$_3$ or —OCH$_2$CH$_2$OCH$_3$.

In the context of the present specification the term "aryl" refers to a ring system which may be mono-, bi- or tricyclic. Examples of such rings include phenyl, naphthalenyl, anthracenyl, indenyl or phenanthrenyl. A preferred aryl group is phenyl.

Unless otherwise indicated, alkenyl and alkynyl, on their own or as part of another substituent, may be straight or branched chain and may preferably contain 2 to 6 carbon atoms, preferably 2 to 4, more preferably 2 to 3, and where appropriate, may be in either the (E)- or (Z)-configuration. Examples include vinyl, allyl and propargyl.

Unless otherwise indicated, cycloalkyl may be mono- or bi-cyclic, may be optionally substituted by one or more C$_1$-C$_6$ alkyl groups, and preferably contain 3 to 7 carbon atoms, more preferably 3 to 6 carbon atoms. Examples of cycloalkyl include cyclopropyl, 1-methylcyclopropyl, 2-methylcyclopropyl, cyclobutyl, cyclopentyl and cyclohexyl.

The term "heterocyclyl" is defined to include heteroaryl and in addition their unsaturated or partially unsaturated analogues such as 4,5,6,7-tetrahydro-benzothiophenyl, 9H-fluorenyl, 3,4-dihydro-2H-benzo-1,4-dioxepinyl, 2,3-dihydro-benzofuranyl, piperidinyl, 1,3-dioxolanyl, 1,3-dioxanyl, 4,5-dihydro-isoxazolyl, tetrahydrofuranyl and morpholinyl.

The term "heteroaryl" refers to an aromatic ring system containing at least one heteroatom and consisting either of a single ring or of two or more fused rings. Preferably, single rings will contain up to three and bicyclic systems up to four heteroatoms which will preferably be chosen from nitrogen, oxygen and sulfur. Examples of such groups include pyridyl, pyridazinyl, pyrimidinyl, pyrazinyl, furanyl, thiophenyl, oxazolyl, isoxazolyl, oxadiazolyl, thiazolyl, isothiazolyl, thiadiazolyl, pyrrolyl, pyrazolyl, imidazolyl, triazolyl and tetrazolyl. A preferred heteroaryl group is pyridine.

Preferred values of W, R$_1$, R$_3$, R$_4$, R$_5$, R$_6$, R$_7$, R$_{10}$, Y and X of the compound of formula I are, in any combination, as set out below:

Y is O or S. More preferably Y is S;

R$_{10}$ is preferably hydrogen, halogen, C$_1$-C$_6$ haloalkyl or cyano. More preferably R$_{10}$ is hydrogen, chlorine, bromine, trifluoromethyl or cyano. In particular, R$_{10}$ is hydrogen.

X is preferably halogen, C$_1$-C$_6$ haloalkyl, cyano, C$_1$-C$_6$ haloalkoxy, C$_1$-C$_6$ haloalkylthio, C$_1$-C$_6$ haloalkylsulfinyl, C$_1$-C$_6$ haloalkylsulfonyl; or X is C$_1$-C$_6$alkoxycarbonyl; or X is heteroaryl or heteroaryl substituted by one or more halogen, cyano, C$_1$-C$_3$ alkyl. In one set of embodiments X is selected from the group consisting of CN, CF$_3$, Cl, Br, Me, CO$_2$Me, CHF$_2$, OMe, and SMe. More preferably X is halogen, C$_1$-C$_6$ haloalkyl or cyano. In a further set of embodiments X is selected from CN CF$_3$, Cl, Br, and I, In particular, X is chlorine, bromine, trifluoromethyl or cyano. In still a further set of embodiments, X is selected from CN, CF$_3$ and Br, R$_1$ is preferably H, C$_1$-C$_6$ alkyl. More preferably R$_1$ is hydrogen, methyl, ethyl or propyl. In particular, R$_1$ is hydrogen.

In one preferred embodiment, R$_2$ is a group according to formula (I')

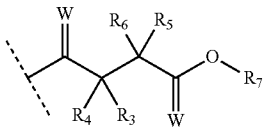

wherein the following substituents are defined independently of one another: each W is independently O or S; more preferably both W are O; R$_3$, R$_4$, R$_5$ and R$_6$ are preferably independently hydrogen, halogen, C$_1$-C$_3$ alkyl, C$_1$-C$_3$ haloalkyl, C$_1$-C$_3$ alkoxy, and hydroxyl. More preferably R$_3$, R$_4$, R$_5$ and R$_6$ are independently hydrogen, methyl, ethyl or isopropyl. In particular R$_3$, R$_4$, R$_5$ and R$_6$ are hydrogen. R$_7$ is hydrogen, C$_1$-C$_6$ alkyl, C$_1$-C$_6$ haloalkyl, C$_2$-C$_6$ alkenyl, C$_2$-C$_6$ haloalkenyl, C$_2$-C$_6$ alkynyl, C$_3$-C$_6$ cycloalkyl, C$_2$-C$_6$ haloalkynyl; aryl or aryl substituted by one to five substituents R$_9$, heterocyclyl or heterocyclyl substituted by one to five substituents R$_9$. More preferably, R$_7$ is hydrogen, C$_1$-C$_6$ alkyl, C$_1$-C$_6$ haloalkyl, C$_2$-C$_6$ alkenyl, C$_2$-C$_6$ alkynyl, or R$_7$ is C$_1$-C$_6$ alkyl substituted by C$_1$-C$_6$ alkoxy or C$_1$-C$_6$ alkylthio or aryl. In one set of embodiments R$_7$ is hydrogen, methyl, CH$_2$CF$_3$, CH$_2$CCH, CH$_2$CH$_2$OCH$_3$, CH$_2$(4-F)Ph, in a further set of embodiments R$_7$ is hydrogen, methyl or benzyl. Each R$_9$ is independently cyano, nitro, amino, hydroxy, halogen, C$_1$-C$_6$ alkyl, C$_1$-C$_6$ haloalkyl, C$_1$-C$_6$ alkoxy, C$_1$-C$_6$ haloalkoxy, C$_1$-C$_6$alkylthio, C$_1$-C$_6$haloalkylthio, C$_1$-C$_6$alkylsulfinyl, C$_1$-C$_6$haloalkylsulfinyl, C$_1$-C$_6$alkylsulfonyl, C$_1$-C$_6$haloalkylsulfonyl, C$_1$-C$_6$ alkylcarbonyl, C$_1$-C$_6$ alkylcarbonyloxy, C$_1$-C$_6$ alkoxycarbonyl, C$_1$-C$_6$ alkylcarbonylamino.

Thus in one preferred embodiment: R$_2$ is the group according to formula (I'); Y is S; both W are O; R$_1$ is H or C$_1$-C$_6$ alkyl; X is halogen, trifluoromethyl or cyano; R$_3$, R$_4$, R$_5$ and R$_6$ are preferably independently hydrogen, halogen, nitro, cyano, C$_1$-C$_3$ alkyl, C$_1$-C$_3$ haloalkyl, C$_1$-C$_3$ alkoxy, or hydroxyl; R$_7$ is hydrogen, C$_1$-C$_6$ alkyl, C$_1$-C$_6$ haloalkyl, C$_2$-C$_6$ alkenyl, C$_2$-C$_6$ alkynyl, or R$_7$ is C$_1$-C$_6$ alkyl substituted by C$_1$-C$_6$ alkoxy or C$_1$-C$_6$ alkylthio or aryl; and R$_{10}$ is preferably hydrogen, halogen, C$_1$-C$_6$ haloalkyl or cyano.

In a further preferred embodiment R$_2$ is the group according to formula (I'); Y is S; both W are O; R$_1$ is H or C$_1$-C$_6$ alkyl; X is methyl, methylcarbonyl, difluoromethyl, Omethyl, or Smethyl; R$_3$, R$_4$, R$_5$ and R$_6$ are preferably independently hydrogen, halogen, nitro, cyano, C$_1$-C$_3$ alkyl, C$_1$-C$_3$ haloalkyl, C$_1$-C$_3$ alkoxy, or hydroxyl; R$_7$ is hydrogen, C$_1$-C$_6$ alkyl, C$_1$-C$_6$ haloalkyl, C$_2$-C$_6$ alkenyl, C$_2$-C$_6$ alkynyl, or R$_7$ is C$_1$-C$_6$ alkyl substituted by C$_1$-C$_6$ alkoxy or C$_r$-C$_6$ alkylthio or aryl; and R$_{10}$ is preferably hydrogen, halogen, C$_1$-C$_6$ haloalkyl or cyano. In each of the above two preferred embodiments preferably, R$_1$ is hydrogen, methyl, ethyl or propyl. More preferably R$_1$ is hydrogen. Preferably, R$_7$ is hydrogen, methyl, CH$_2$CF$_3$, CH$_2$CCH, CH$_2$CH$_2$OCH$_3$, CH$_2$(4-F)Ph, or in the alternative R$_7$ is preferably hydrogen, methyl, ethyl or benzyl. Preferably, X is bromine, chlorine, trifluoromethyl or cyano. Preferably, R$_3$, R$_4$, R$_5$ and R$_6$ are independently hydrogen or C$_1$-C$_3$ alkyl, preferably hydrogen. Preferably, R$_{10}$ is hydrogen, chlorine, bromine, trifluoromethyl or cyano, preferably hydrogen. In another preferred embodiment R$_1$ and R$_2$ form a cyclic group around the nitrogen

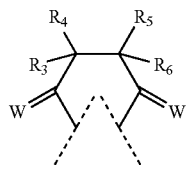

(I″)

wherein W, $R_3$, $R_4$, $R_5$ and $R_6$ are as defined supra, including the definitions of the preferred and most preferred substituents above.

In another preferred embodiment A is —NHCN, so that $R_2$ has formula (I‴)

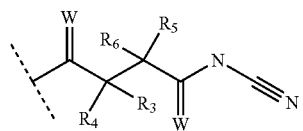

(I‴)

wherein W, $R_3$, $R_4$, $R_5$ and $R_6$ are as defined supra, including the definitions of the preferred and most preferred substituents above.

Table 1 below includes examples of compounds of formula (Ia) wherein W is O, Y is S, $R_1$ is H, $R_{10}$, X, $R_3$, $R_4$, $R_5$, $R_6$, $R_7$ are as defined in the table.

TABLE 1

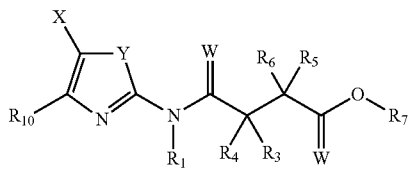

(Ia)

| Compound | X | R10 | $R_3$ | $R_4$ | $R_5$ | $R_6$ | $R_7$ |
|---|---|---|---|---|---|---|---|
| 1.00 | Cl | H | H | H | H | H | H |
| 1.01 | Br | H | H | H | H | H | H |
| 1.02 | $CF_3$ | H | H | H | H | H | H |
| 1.03 | CN | H | H | H | H | H | H |
| 1.04 | I | H | H | H | H | H | H |
| 1.05 | I | H | H | H | H | H | $CH_3$ |
| 1.06 | Cl | H | H | H | H | H | $CH_3$ |
| 1.07 | Br | H | H | H | H | H | $CH_3$ |
| 1.08 | $CF_3$ | H | H | H | H | H | $CH_3$ |
| 1.09 | CN | H | H | H | H | H | $CH_3$ |
| 1.10 | Cl | H | H | H | H | H | $CH_2Ph$ |
| 1.11 | Br | H | H | H | H | H | $CH_2Ph$ |
| 1.12 | $CF_3$ | H | H | H | H | H | $CH_2Ph$ |
| 1.13 | CN | H | H | H | H | H | $CH_2Ph$ |
| 1.14 | I | H | H | H | H | H | $CH_2Ph$ |

Table 2 below includes examples of compounds of formula (Ib) wherein W is O, Y is S, $R_{10}$, X, $R_3$, $R_4$, $R_5$, $R_6$ are as defined.

TABLE 2

(Ib)

| Compound | X | R10 | $R_3$ | $R_4$ | $R_5$ | $R_6$ |
|---|---|---|---|---|---|---|
| 2.00 | Cl | H | H | H | H | H |
| 2.01 | Br | H | H | H | H | H |
| 2.02 | I | H | H | H | H | H |
| 2.03 | CF3 | H | H | H | H | H |
| 2.04 | CN | H | H | H | H | H |

Table 3 below includes examples of compounds of formula (Iz) wherein A is —NHCN, W is O, Y is S, R1 is H, R10, X, R3, R4, R5, R6, R7 are as defined in the table.

TABLE 3

(Iz)

| Compound | X | R10 | $R_3$ | $R_4$ | $R_5$ | $R_6$ |
|---|---|---|---|---|---|---|
| 3.00 | Cl | H | H | H | H | H |
| 3.01 | Br | H | H | H | H | H |
| 3.02 | $CF_3$ | H | H | H | H | H |
| 3.03 | CN | H | H | H | H | H |
| 3.04 | I | H | H | H | H | H |

The compounds of Formula (I) according to the invention can be used as plant growth regulators or seed germination promoters by themselves, but they are generally formulated into plant growth regulation or seed germination promotion compositions using formulation adjuvants, such as carriers, solvents and surface-active agents (SFAs). Thus, the present invention further provides a plant growth regulator composition comprising a plant growth regulation compound as described herein (including the compounds according to formula (i) to (viii)) and an agriculturally acceptable formulation adjuvant or carrier. The present invention further provides a seed germination promoter composition comprising a seed germination promoter compound as described herein and an agriculturally acceptable formulation adjuvant or carrier. Preferably the composition consists essentially of a compound of Formula (I) and an agriculturally acceptable formulation adjuvant or carrier. In the alternative, the composition consists of a compound of Formula (I) and at least one agriculturally acceptable formulation adjuvant or carrier.

In one embodiment, the present invention provides a composition comprising a compound of Formula (I) and an agriculturally acceptable carrier, wherein in Formula I, $R_2$ is the group according to formula (I'); Y is S; Both W are O; $R_1$ is H or $C_1$-$C_6$ alkyl; X is halogen, trifluoromethyl or cyano; $R_3$, $R_4$, $R_5$ and $R_6$ are preferably independently hydrogen, halogen, nitro, cyano, $C_1$-$C_3$ alkyl, $C_1$-$C_3$ haloalkyl, $C_1$-$C_3$ alkoxy, or hydroxyl; $R_7$ is hydrogen, $C_1$-$C_6$ alkyl, $C_1$-$C_6$ haloalkyl, $C_2$-$C_6$ alkenyl, $C_2$-$C_6$ alkynyl, or $R_7$ is $C_1$-$C_6$ alkyl substituted by $C_1$-$C_6$ alkoxy, $C_1$-$C_6$ alkylthio or aryl; and $R_{10}$ is preferably hydrogen, halogen, $C_1$-$C_6$ haloalkyl or cyano.

Preferably, $R_1$ is hydrogen, methyl, ethyl or propyl, more preferably hydrogen.

Preferably, $R_7$ is hydrogen, methyl, ethyl or benzyl.

Preferably, X is bromine, chlorine, trifluoromethyl or cyano.

Preferably, $R_3$, $R_4$, $R_5$ and $R_6$ are independently hydrogen or $C_1$-$C_3$ alkyl, more preferably hydrogen.

Preferably, $R_{10}$ is hydrogen, chlorine, bromine, trifluoromethyl or cyano, more preferably hydrogen.

The skilled man will appreciate that any and/or all combinations of the preferred and more preferred substituents as described herein are hereby also disclosed.

In another embodiment, the present invention provides a composition comprising a compound of Formula (I) and an agriculturally acceptable carrier, wherein in Formula (I), $R_1$ and $R_2$ form a cyclic group around the nitrogen according to formula (I''); Y is S; both W are O; X is halogen, trifluoromethyl or cyano; $R_3$, $R_4$, $R_5$ and $R_6$ are preferably independently hydrogen, halogen, nitro, cyano, $C_1$-$C_3$ alkyl, $C_1$-$C_3$ haloalkyl, $C_1$-$C_3$ alkoxy, or hydroxyl; and $R_{10}$ is preferably hydrogen, halogen, $C_1$-$C_6$ haloalkyl or cyano.

Preferably, X is bromine, chlorine, trifluoromethyl or cyano.

Preferably, $R_3$, $R_4$, $R_5$ and $R_6$ are independently hydrogen or $C_1$-$C_3$ alkyl, more preferably hydrogen.

Preferably, $R_{10}$ is hydrogen, chlorine, bromine, trifluoromethyl or cyano, more preferably hydrogen.

The skilled man will appreciate that any and/or all combinations of the preferred and more preferred substituents as described herein are hereby also disclosed.

In another embodiment, the present invention provides a composition comprising a compound of Formula (I) and an agriculturally acceptable carrier, wherein in Formula (I), $R_2$ is the group according to formula (I''); Y is S; both W are O; $R_1$ is H or $C_1$-$C_6$ alkyl; X is halogen, trifluoromethyl or cyano; $R_3$, $R_4$, $R_5$ and $R_6$ are preferably independently hydrogen, halogen, nitro, cyano, $C_1$-$C_3$ alkyl, $C_1$-$C_3$ haloalkyl, $C_1$-$C_3$ alkoxy, or hydroxyl; and $R_{10}$ is preferably hydrogen, halogen, $C_1$-$C_6$ haloalkyl or cyano.

Preferably, $R_1$ is hydrogen, methyl, ethyl or propyl, more preferably hydrogen.

Preferably, X is bromine, chlorine, trifluoromethyl or cyano.

Preferably, $R_3$, $R_4$, $R_5$ and $R_6$ are independently hydrogen or $C_1$-$C_3$ alkyl, more preferably hydrogen.

Preferably, $R_{10}$ is hydrogen, chlorine, bromine, trifluoromethyl or cyano, more preferably hydrogen.

The skilled man will appreciate that any and/or all combinations of the preferred and more preferred substituents as described herein are hereby also disclosed.

The composition can be in the form of concentrates which are diluted prior to use, although ready-to-use compositions can also be made. The final dilution is usually made with water, but can be made instead of, or in addition to, water, with, for example, liquid fertilisers, micronutrients, biological organisms, oil or solvents.

The compositions generally comprise from 0.1 to 99% by weight, especially from 0.1 to 95% by weight, compounds of Formula I and from 1 to 99.9% by weight of a formulation adjuvant which preferably includes from 0 to 25% by weight of a surface-active substance. Compositions of the invention as described above, which include surface-active substances also include compounds of Formula (I) as defined by formula (i), (ii), (iii), (iv), (v), (vi), (vii), and (viii) defined supra.

The compositions can be chosen from a number of formulation types, many of which are known from the Manual on Development and Use of FAO Specifications for Plant Protection Products, 5th Edition, 1999. These include dustable powders (DP), soluble powders (SP), water soluble granules (SG), water dispersible granules (WG), wettable powders (WP), granules (GR) (slow or fast release), soluble concentrates (SL), oil miscible liquids (OL), ultra-low volume liquids (UL), emulsifiable concentrates (EC), dispersible concentrates (DC), emulsions (both oil in water (EW) and water in oil (EO)), micro-emulsions (ME), suspension concentrates (SC), aerosols, capsule suspensions (CS) and seed treatment formulations. The formulation type chosen in any instance will depend upon the particular purpose envisaged and the physical, chemical and biological properties of the compound of Formula (I).

Dustable powders (DP) may be prepared by mixing a compound of Formula (I) with one or more solid diluents (for example natural clays, kaolin, pyrophyllite, bentonite, alumina, montmorillonite, kieselguhr, chalk, diatomaceous earths, calcium phosphates, calcium and magnesium carbonates, sulphur, lime, flours, talc and other organic and inorganic solid carriers) and mechanically grinding the mixture to a fine powder.

Soluble powders (SP) may be prepared by mixing a compound of Formula (I) with one or more water-soluble inorganic salts (such as sodium bicarbonate, sodium carbonate or magnesium sulphate) or one or more water-soluble organic solids (such as a polysaccharide) and, optionally, one or more wetting agents, one or more dispersing agents or a mixture of said agents to improve water dispersibility/solubility. The mixture is then ground to a fine powder. Similar compositions may also be granulated to form water soluble granules (SG).

Wettable powders (WP) may be prepared by mixing a compound of Formula (I) with one or more solid diluents or carriers, one or more wetting agents and, preferably, one or more dispersing agents and, optionally, one or more suspending agents to facilitate the dispersion in liquids. The mixture is then ground to a fine powder. Similar compositions may also be granulated to form water dispersible granules (WG).

Granules (GR) may be formed either by granulating a mixture of a compound of Formula (I) and one or more powdered solid diluents or carriers, or from pre-formed blank granules by absorbing a compound of Formula (I) (or a solution thereof, in a suitable agent) in a porous granular material (such as pumice, attapulgite clays, fuller's earth, kieselguhr, diatomaceous earths or ground corn cobs) or by adsorbing a compound of Formula (I) (or a solution thereof, in a suitable agent) on to a hard core material (such as sands, silicates, mineral carbonates, sulphates or phosphates) and drying if necessary. Agents which are commonly used to aid absorption or adsorption include solvents (such as aliphatic and aromatic petroleum solvents, alcohols, ethers, ketones and esters) and sticking agents (such as polyvinyl acetates, polyvinyl alcohols, dextrins, sugars and vegetable oils). One or more other additives may also be included in granules (for example an emulsifying agent, wetting agent or dispersing agent).

Dispersible Concentrates (DC) may be prepared by dissolving a compound of Formula (I) in water or an organic solvent, such as a ketone, alcohol or glycol ether. These solutions may contain a surface active agent (for example to improve water dilution or prevent crystallisation in a spray tank).

Emulsifiable concentrates (EC) or oil-in-water emulsions (EW) may be prepared by dissolving a compound of Formula (I) in an organic solvent (optionally containing one or more wetting agents, one or more emulsifying agents or a mixture of said agents). Suitable organic solvents for use in ECs include aromatic hydrocarbons (such as alkylbenzenes or alkylnaphthalenes, exemplified by SOLVESSO 100, SOLVESSO 150 and SOLVESSO 200; SOLVESSO is a Registered Trade Mark), ketones (such as cyclohexanone or methylcyclohexanone) and alcohols (such as benzyl alcohol, furfuryl alcohol or butanol), N-alkylpyrrolidones (such as N-methylpyrrolidone or N-octylpyrrolidone), dimethyl amides of fatty acids (such as $C_8$-$C_{10}$ fatty acid dimethylamide) and chlorinated hydrocarbons. An EC product may spontaneously emulsify on addition to water, to produce an emulsion with sufficient stability to allow spray application through appropriate equipment.

Preparation of an EW involves obtaining a compound of Formula (I) either as a liquid (if it is not a liquid at room temperature, it may be melted at a reasonable temperature, typically below 70° C.) or in solution (by dissolving it in an appropriate solvent) and then emulsifying the resultant liquid or solution into water containing one or more SFAs, under high shear, to produce an emulsion. Suitable solvents for use in EWs include vegetable oils, chlorinated hydrocarbons (such as chlorobenzenes), aromatic solvents (such as alkylbenzenes or alkylnaphthalenes) and other appropriate organic solvents which have a low solubility in water.

Microemulsions (ME) may be prepared by mixing water with a blend of one or more solvents with one or more SFAs, to produce spontaneously a thermodynamically stable isotropic liquid formulation. A compound of Formula (I) is present initially in either the water or the solvent/SFA blend. Suitable solvents for use in MEs include those hereinbefore described for use in ECs or in EWs. An ME may be either an oil-in-water or a water-in-oil system (which system is present may be determined by conductivity measurements) and may be suitable for mixing water-soluble and oil-soluble pesticides in the same formulation. An ME is suitable for dilution into water, either remaining as a microemulsion or forming a conventional oil-in-water emulsion.

Suspension concentrates (SC) may comprise aqueous or non-aqueous suspensions of finely divided insoluble solid particles of a compound of Formula (I). SCs may be prepared by ball or bead milling the solid compound of Formula (I) in a suitable medium, optionally with one or more dispersing agents, to produce a fine particle suspension of the compound. One or more wetting agents may be included in the composition and a suspending agent may be included to reduce the rate at which the particles settle. Alternatively, a compound of Formula (I) may be dry milled and added to water, containing agents hereinbefore described, to produce the desired end product.

Aerosol formulations comprise a compound of Formula (I) and a suitable propellant (for example n-butane). A compound of Formula (I) may also be dissolved or dispersed in a suitable medium (for example water or a water miscible liquid, such as n-propanol) to provide compositions for use in non-pressurised, hand-actuated spray pumps.

Capsule suspensions (CS) may be prepared in a manner similar to the preparation of EW formulations but with an additional polymerisation stage such that an aqueous dispersion of oil droplets is obtained, in which each oil droplet is encapsulated by a polymeric shell and contains a compound of Formula (I) and, optionally, a carrier or diluent therefor. The polymeric shell may be produced by either an interfacial polycondensation reaction or by a coacervation procedure. The compositions may provide for controlled release of the compound of Formula (I) and they may be used for seed treatment. A compound of Formula (I) may also be formulated in a biodegradable polymeric matrix to provide a slow, controlled release of the compound.

The composition may include one or more additives to improve the biological performance of the composition, for example by improving wetting, retention or distribution on surfaces; resistance to rain on treated surfaces; or uptake or mobility of a compound of Formula (I). Such additives include surface active agents (SFAs), spray additives based on oils, for example certain mineral oils or natural plant oils (such as soy bean and rape seed oil), and blends of these with other bio-enhancing adjuvants (ingredients which may aid or modify the action of a compound of Formula (I)).

Wetting agents, dispersing agents and emulsifying agents may be SFAs of the cationic, anionic, amphoteric or non-ionic type.

Suitable SFAs of the cationic type include quaternary ammonium compounds (for example cetyltrimethyl ammonium bromide), imidazolines and amine salts.

Suitable anionic SFAs include alkali metals salts of fatty acids, salts of aliphatic monoesters of sulphuric acid (for example sodium lauryl sulphate), salts of sulphonated aromatic compounds (for example sodium dodecylbenzenesulphonate, calcium dodecylbenzenesulphonate, butylnaphthalene sulphonate and mixtures of sodium di-isopropyl- and tri-isopropyl-naphthalene sulphonates), ether sulphates, alcohol ether sulphates (for example sodium laureth-3-sulphate), ether carboxylates (for example sodium laureth-3-carboxylate), phosphate esters (products from the reaction between one or more fatty alcohols and phosphoric acid (predominately mono-esters) or phosphorus pentoxide (predominately di-esters), for example the reaction between lauryl alcohol and tetraphosphoric acid; additionally these products may be ethoxylated), sulphosuccinamates, paraffin or olefine sulphonates, taurates and lignosulphonates.

Suitable SFAs of the amphoteric type include betaines, propionates and glycinates.

Suitable SFAs of the non-ionic type include condensation products of alkylene oxides, such as ethylene oxide, propylene oxide, butylene oxide or mixtures thereof, with fatty alcohols (such as oleyl alcohol or cetyl alcohol) or with alkylphenols (such as octylphenol, nonylphenol or octylcresol); partial esters derived from long chain fatty acids or hexitol anhydrides; condensation products of said partial esters with ethylene oxide; block polymers (comprising ethylene oxide and propylene oxide); alkanolamides; simple esters (for example fatty acid polyethylene glycol esters); amine oxides (for example lauryl dimethyl amine oxide); and lecithins.

Suitable suspending agents include hydrophilic colloids (such as polysaccharides, polyvinylpyrrolidone or sodium carboxymethylcellulose) and swelling clays (such as bentonite or attapulgite).

The present invention still further provides a method for regulating the growth of plants in a locus, wherein the method comprises application to the locus of a plant growth regulating amount of a composition or compound (i.e. formula (I) including compounds according to formula (i) to (viii) above) according to the present invention. Preferably the composition or compound is applied by spray application to the leaves of the plant.

The present invention also provides a method for promoting the germination of seeds, comprising applying to the seeds, or to a locus containing seeds, a seed germination promoting amount of a composition or compound (i.e. formula (I) including compounds according to formula (i) to (viii) above) according to the present invention.

The application is generally made by spraying the composition, typically by tractor mounted sprayer for large areas, but other methods such as dusting (for powders), drip or drench can also be used. Alternatively the composition may be applied in furrow or directly to a seed before or at the time of planting.

The compound of formula (I) (i.e. formula (I) including compounds according to formula (i) to (viii) above) or composition of the present invention may be applied to a plant, part of the plant, plant organ, plant propagation material or a surrounding area thereof.

In one embodiment, the invention relates to a method of treating a plant propagation material comprising applying to the plant propagation material a composition of the present invention in an amount effective to promote germination and/or regulate plant growth. The invention also relates to a plant propagation material treated with a compound of formula (I) (i.e. formula (I) including compounds according to formula (i) to (viii) above) or a composition of the present invention. Preferably, the plant propagation material is a seed.

The term "plant propagation material" denotes all the generative parts of the plant, such as seeds, which can be used for the multiplication of the latter and vegetative plant materials such as cuttings and tubers. In particular, there may be mentioned the seeds, roots, fruits, tubers, bulbs, and rhizomes.

Methods for applying active ingredients to plant propagation material, especially seeds, are known in the art, and include dressing, coating, pelleting and soaking application methods of the propagation material. The treatment can be applied to the seed at any time between harvest of the seed and sowing of the seed or during the sowing process. The seed may also be primed either before or after the treatment. The compound of formula (I) (i.e. formula (I) including compounds according to formula (i) to (viii) above) may optionally be applied in combination with a controlled release coating or technology so that the compound is released over time.

The composition of the present invention may be applied pre-emergence or post-emergence. Suitably, where the composition is being used to regulate the growth of crop plants, it may be applied pre or post-emergence, but preferably post-emergence of the crop. Where the composition is used to promote the germination of seeds, it may be applied pre-emergence.

The rates of application of compounds of Formula I (i.e. formula (I) including compounds according to formula (i) to (viii) above) may vary within wide limits and depend on the nature of the soil, the method of application (pre- or post-emergence; seed dressing; application to the seed furrow; no tillage application etc.), the crop plant, the prevailing climatic conditions, and other factors governed by the method of application, the time of application and the target crop. For foliar or drench application, the compounds of Formula I according to the invention are generally applied at a rate of from 0.001 to 2000 g/ha, especially from 0.01 to 400 g/ha. For seed treatment the rate of application is generally between 0.0005 and 150 g per 100 kg of seed.

Plants in which the composition according to the invention can be used include crops such as cereals (for example wheat, barley, rye, oats); beet (for example sugar beet or fodder beet); fruits (for example pomes, stone fruits or soft fruits, such as apples, pears, plums, peaches, almonds, cherries, strawberries, raspberries or blackberries); leguminous plants (for example beans, lentils, peas or soybeans); oil plants (for example rape, mustard, poppy, olives, sunflowers, coconut, castor oil plants, cocoa beans or groundnuts); cucumber plants (for example marrows, cucumbers or melons); fibre plants (for example cotton, flax, hemp or jute); citrus fruit (for example oranges, lemons, grapefruit or mandarins); vegetables (for example spinach, lettuce, asparagus, cabbages, carrots, onions, tomatoes, potatoes, cucurbits or paprika); lauraceae (for example avocados, cinnamon or camphor); maize; rice; tobacco; nuts; coffee; sugar cane; tea; vines; hops; durian; bananas; natural rubber plants; turf or ornamentals (for example flowers, shrubs, broad-leaved trees or evergreens such as conifers). This list does not represent any limitation.

The invention may also be used to regulate the growth, or promote the germination of seeds of non-crop plants, for example to facilitate weed control by synchronizing germination.

Crops are to be understood as also including those crops which have been modified by conventional methods of breeding or by genetic engineering. For example, the invention may be used in conjunction with crops that have been rendered tolerant to herbicides or classes of herbicides (e.g. ALS-, GS-, EPSPS-, PPO-, ACCase- and HPPD-inhibitors). An example of a crop that has been rendered tolerant to imidazolinones, e.g. imazamox, by conventional methods of breeding is Clearfield® summer rape (canola). Examples of crops that have been rendered tolerant to herbicides by genetic engineering methods include e.g. glyphosate- and glufosinate-resistant maize varieties commercially available under the trade names RoundupReady® and LibertyLink®. Methods of rending crop plants tolerant to HPPD-inhibitors are known, for example from WO0246387; for example the crop plant is transgenic in respect of a polynucleotide comprising a DNA sequence which encodes an HPPD-inhibitor resistant HPPD enzyme derived from a bacterium, more particularly from *Pseudomonas fluorescens* or *Shewanella colwelliana*, or from a plant, more particularly, derived from a monocot plant or, yet more particularly, from a barley, maize, wheat, rice, *Brachiaria*, *Chenchrus*, *Lolium*, *Festuca*, *Setaria*, *Eleusine*, *Sorghum* or *Avena* species.

Crops are also to be understood as being those which have been rendered resistant to harmful insects by genetic engineering methods, for example Bt maize (resistant to European corn borer), Bt cotton (resistant to cotton boll weevil) and also Bt potatoes (resistant to Colorado beetle). Examples of Bt maize are the Bt 176 maize hybrids of NK® (Syngenta Seeds). The Bt toxin is a protein that is formed naturally by *Bacillus thuringiensis* soil bacteria. Examples of toxins, or transgenic plants able to synthesise such toxins, are described in EP-A-451 878, EP-A-374 753, WO 93/07278, WO 95/34656, WO 03/052073 and EP-A-427 529. Examples of transgenic plants comprising one or more genes that code for an insecticidal resistance and express one or more toxins are KnockOut® (maize), Yield Gard® (maize), NuCOTIN33B® (cotton), Bollgard® (cotton), NewLeaf® (potatoes), NatureGard® and Protexcta®. Plant crops or seed material thereof can be both resistant to herbicides and, at the same time, resistant to insect feeding ("stacked" transgenic events). For example, seed can have the ability to express an insecticidal Cry3 protein while at the same time being tolerant to glyphosate.

Crops are also to be understood to include those which are obtained by conventional methods of breeding or genetic engineering and contain so-called output traits (e.g. improved storage stability, higher nutritional value and improved flavour).

Compounds of the present invention may be in the form of an ester or an acid, either of which may have plant growth regulating properties. As suggested in WO2009/109570, it is thought that the ester form of the compounds of Formula I may be hydrolysed in planta to the acid form. This may be a particular advantage where the esterified compounds are more readily taken up by the plant, for example through leaf tissue.

Compounds and compositions of the present invention may be applied in combination with other active ingredients or products for use in agriculture, including insecticides, fungicides, herbicides, plant growth regulators, crop enhancing compounds, nutrients and biologicals. Examples of suitable mixing partners may be found in the Pesticide Manual, 15$^{th}$ edition (published by the British Crop Protection Council). Such mixtures may be applied to a plant, plant propagation material or plant growing locus either simultaneously (for example as a pre-formulated mixture or a tank mix), or sequentially in a suitable timescale. Co-application of pesticides with the present invention has the added benefit of minimising farmer time spent applying products to crops.

In a further aspect of the present invention, the compounds or composition of the present invention may be applied in combination with one or more other compounds having a crop enhancement effect. Such compounds include micronutrients, saccharides, amino acids, flavonoids, quinines, and plant activators/growth stimulators. For example, such compounds include natural or synthetic hormones, auxins, brassinosteroids, gibberellins, abscisic acid, cytokinins, jasmonates, strigolactones, salicylic acid, ethylene, 1-methylcyclopropene, trinexapac-ethyl or derivatives thereof. Such compounds also include pesticides that have a crop enhancement effect, for example strobilurins (including azoxystrobin, pyraclostrobin), and neonicotinoids (including thiamethoxam, and imidacloprid). The compounds according to the invention or a composition, comprising a compound according to the invention, can also be used as herbicides. The invention thus also covers a method for killing weeds and unwanted vegetation, wherein the method comprises applying to said weeds or unwanted vegetation an amount of a compound or a composition according to the invention. The invention thus also covers a method for controlling weeds comprising applying to weeds post-emergence an effective amount of a compound or a composition according to the invention. The invention thus also covers a method for controlling weeds comprising applying to the soil before said weeds emerge an effective amount of a compound or a composition according to the invention.

The compounds of the invention may be made by the following methods.

SCHEME 1

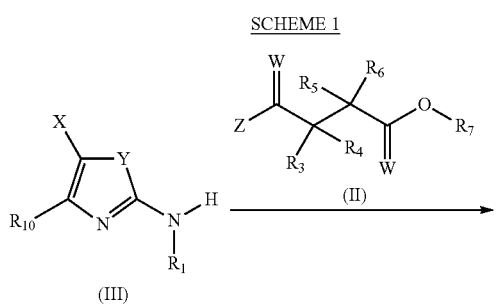

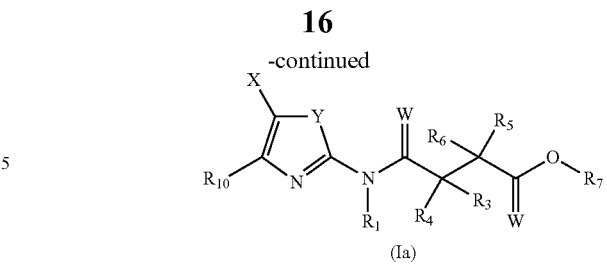

Compounds of formula (Ia) may be prepared from a compound of formula (III) via acylation by reaction of a compounds of formula (II) within Z is halogen such as chlorine, such reactions are usually carried out in the presence of a base, and optionally in the presence of a nucleophilic catalyst. Alternatively, it is possible to conduct the reaction in a biphasic system comprising an organic solvent, preferably ethyl acetate, and an aqueous solvent, preferably a solution of sodium hydrogen carbonate.

Compounds of formula (II) are commercially available, such as methyl succinate chloride or can be made by methods known to a person skilled in the art.

SCHEME 2

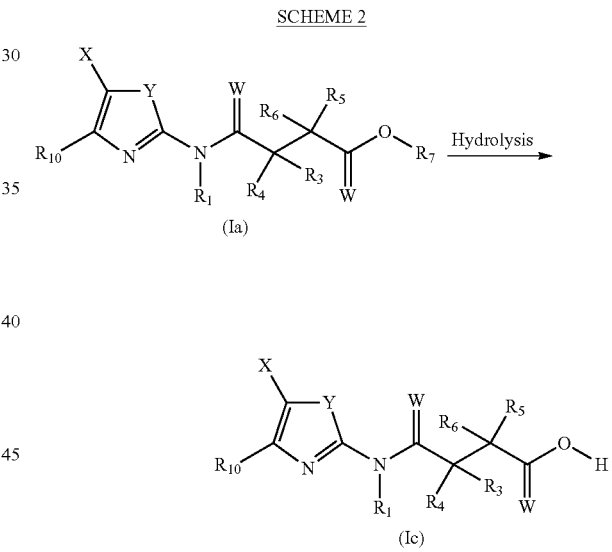

Compounds of formula (Ic) may be made by treatment of compounds of formula (Ia), wherein $R_7$ is not hydrogen, by hydrolysis of the ester group under standard conditions, such as treatment with an alkali hydroxide, such as sodium hydroxide or potassium hydroxide, in a solvent, such as ethanol or tetrahydrofuran, in the presence of water. Another alternative is the treatment of the ester of formula (Ia) with an acid, such as trifluoroacetic acid, in a solvent, such as dichloromethane, followed by addition of water. The reaction is carried out preferably at a temperature of from −20° C. to +100° C., more preferably from 20° C. to 80° C., in particular at 50° C.

SCHEME 3

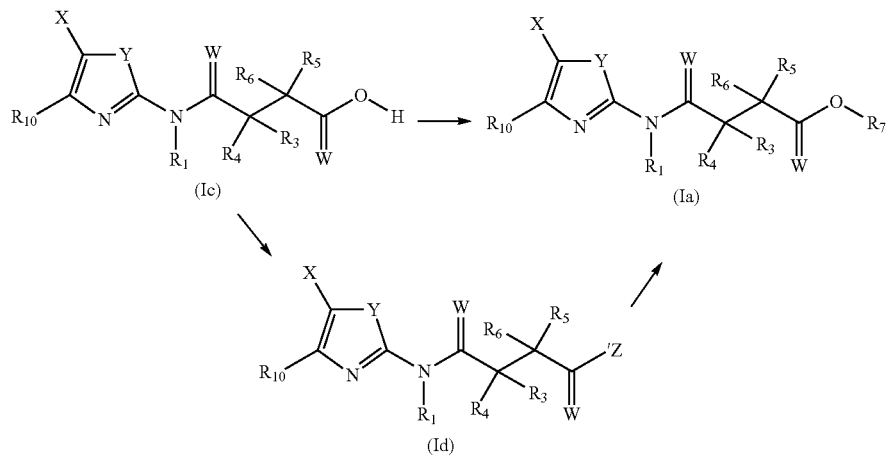

Compounds of formula (Ia) wherein R₇ is not hydrogen may be prepared from a compound of formula (Ic) via esterification by reaction of a alcohol derivative in the presence of a coupling reagent, such as DCC (N,N'-Dicyclohexylcarbodiimide), EDC (1-ethyl-3-[3-dimethylaminopropyl]carbodiimide hydrochloride) or BOP—Cl (bis(2-oxo-3-oxazolidinyl)phosphonic chloride), in the presence of a base, such as pyridine, triethylamine, 4-(dimethylamino) pyridine or diisopropylethylamine, and optionally in the presence of a nucleophilic catalyst, such as hydroxybenzotriazole.

Alternatively, Compounds of formula (Ia) may be prepared from a compound of formula (Id), wherein Z is a leaving group such as chlorine. The reaction may be carried out under basic conditions (for example in the presence of pyridine, triethylamine, 4-(dimethylamino)pyridine or diisopropylethylamine) and in a suitable solvent, such as, for instance, tetrahydrofuran, optionally in the presence of a nucleophilic catalyst. The reaction is carried out at a temperature of from −120° C. to +130° C., preferably from −100° C. to 100° C. Alternatively, the reaction may be conducted in a biphasic system comprising an organic solvent, preferably ethyl acetate, and an aqueous solvent, preferably a saturated solution of sodium bicarbonate.

Compounds of formula (Id) may be prepared from a compound of formula (Ic), under standard conditions, such as treatment with thionyl chloride or oxalyl chloride, in a solvent, such as dichloromethane. The reaction is carried out preferably at a temperature of from −20° C. to +100° C., more preferably from 0° C. to 50° C., in particular at ambient temperature.

SCHEME 4

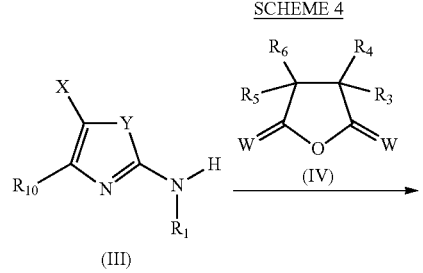

-continued

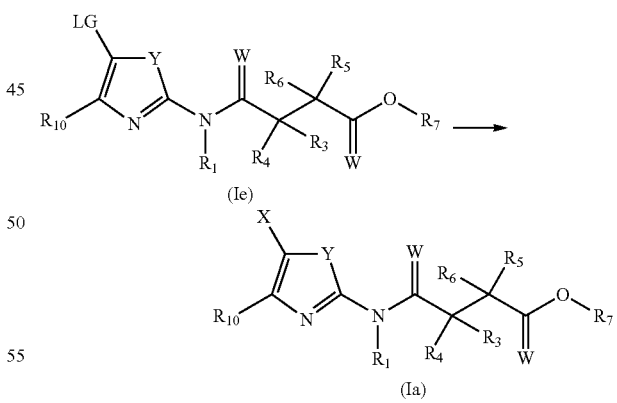

Compounds of formula (Ic) may be made by treatment of compounds of formula (III) by treatment with a anhydride derivatives of formula (IV), such as succinic anhydride, in a solvent, such as tetrahydrofuran. The reaction is carried out preferably at a temperature from −20° C. to +120° C., more preferably from 20° C. to 120° C.

SCHEME 5

Compounds of Formula (Ia) wherein X is aryl, heteroaryl or $C_3$-$C_8$cycloalkyl derivatives such as thiophen, vinyl, allyl or cyclopropyl can be prepared by the reaction of compounds of formula (Ie) wherein LG is a suitable leaving group, such as, for example halogen or triflate with a derivative of formula Z—X, wherein Z is a boron or a tin derivatives and X is as described for the compound of Formula (I) in the presence of a suitable catalyst/ligand system, often a palladium (0) complex and in the presence or not of a base such as potassium carbonate. These reactions can be carried out or not under microwave irradiation. These reactions being known to the person skilled in the art under the name of Stille, Suzuki coupling sees for example: Strategic Applications of Named Reactions in Organic Synthesis Kurti, Laszlo; Czako, Barbara; Editors. USA. (2005), Publisher: Elsevier Academic Press, Burlington, Mass. p. 448 (Suzuki coupling) and p. 438 (Stille coupling) and cited references.

SCHEME 6

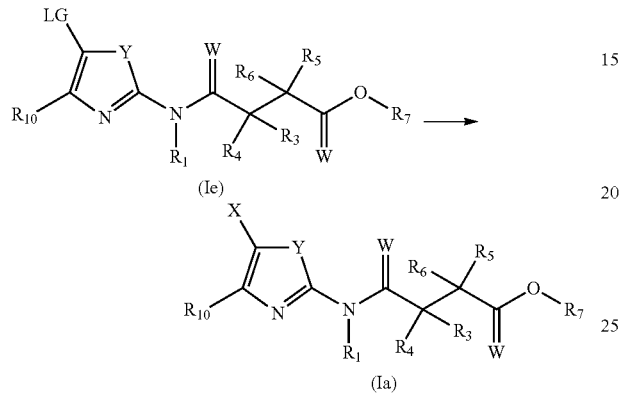

Compounds of Formula (Ia) wherein X is CCR where R is an $C_1$-$C_6$ alkyl, H or trialkyl silyl can be prepared by the reaction of compounds of formula (Ie) wherein LG is a suitable leaving group such as for example halogen or triflate with a derivative of formula HCCR in the presence of a suitable catalyst/ligand system, often a palladium (0) complex with or without a source of copper such as copper iodide and an organic base such as diisopropylethyl amine. This reaction being known to the person skilled in the art under the name of Sonogashira coupling, see for example: Strategic Applications of Named Reactions in Organic Synthesis Kurti, Laszlo; Czako, Barbara; Editors. USA. (2005), Publisher: Elsevier Academic Press, Burlington, Mass. p. 424 (Sonogashira coupling) and cited references. Compounds of Formula (Ia) wherein X is CCH can be prepared by the reaction of compounds of formula (Ia) type wherein X is CCSiR$_3$ where R is a C1-C6 alkyl group by reaction with a base such as potassium carbonate of a fluoride source such as potassium fluoride.

SCHEME 7

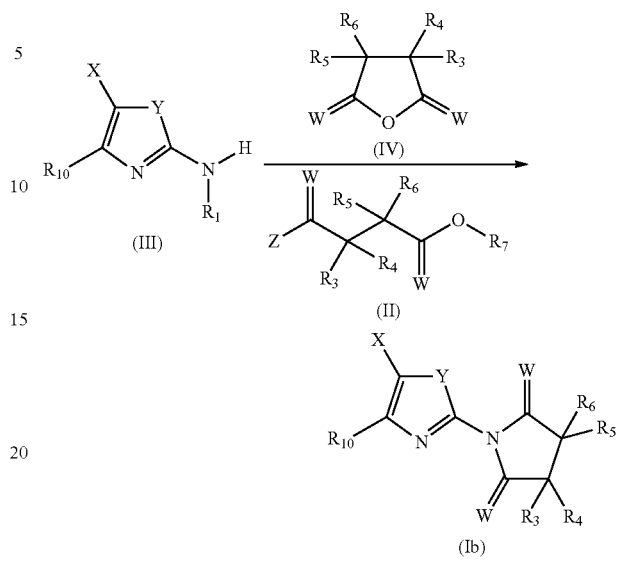

Compounds of Formula (Ib) may be prepared, in one step from a compound of Formula (III), wherein R1 is H, by reaction in the presence of compound of Formula (II) by heating, optionally in the presence of an acid, such as acetic acid or a base, such as triethylamine. These reactions are well known by a person skilled in the art. See for few literature examples: Journal of Fluorine Chemistry (2006), 127(3), 417-425 or Tetrahedron Letters (2005), 46(5), 759-762.

Alternatively, compounds of Formula (Ib) may be prepared, in one step from a compound of Formula (III) by reaction in the presence of compound of Formula (IV) by heating, optionally in the presence of an acid, such as acetic acid or a base, such as triethylamine. These reaction are well known by a person skilled in the art. See for few literature example: Organic Letters (2011), 13(16), 4320-4323, Pharma Chemica (2011), 3(2), 283-286, journal of Medicinal Chemistry (2007), 50(6), 1124-1132, Journal of the American Chemical Society (2006), 128(14), 4892-4901 or European Journal of Medicinal Chemistry (2011), 46(9), 4324-4329.

SCHEME 8

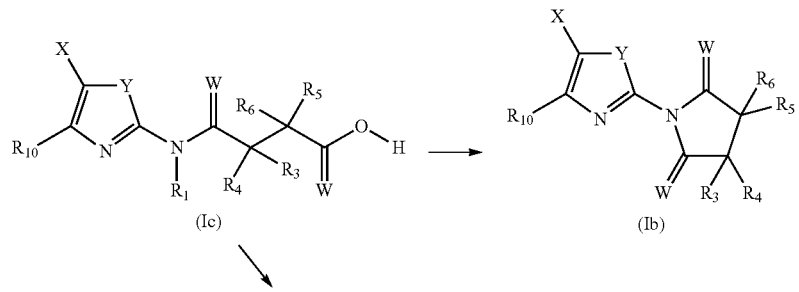

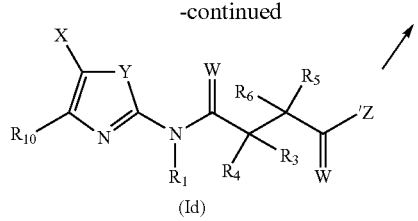

(Id)

Compounds of Formula (Ib) may be prepared from a compound of Formula (Ic) by reaction in the presence of a coupling reagent, such as diimidazolyl ketone, DCC (N,N'-dicyclohexylcarbodiimide), EDCI (1-Ethyl-3-(3-dimethyl-aminopropyl)carbodiimide monohydrochloride) or BOP—Cl (bis(2-oxo-3-oxazolidinyl)phosphonic chloride), optionally in the presence of a base, such as pyridine, triethylamine, 4-(dimethylamino)pyridine or diisopropyl-ethylamine, and optionally in the presence of a nucleophilic catalyst, such as hydroxybenzotriazole. Alternatively, compounds of Formula (Ib) may be prepared from a compound of Formula (Ic) by reaction in the presence of anhydride or acid chloride derivatives such as acetic anhydride or phenyl optionally in presence of a base such as sodium acetate.

Alternatively, compounds of Formula (Ib) may be prepared from a compound of Formula (Ic) via acid halides of formula (Id), wherein Z is a leaving group such as chlorine by reaction of compound (Ic) under standard conditions, such as treatment with thionyl chloride or oxalyl chloride.

Scheme 9

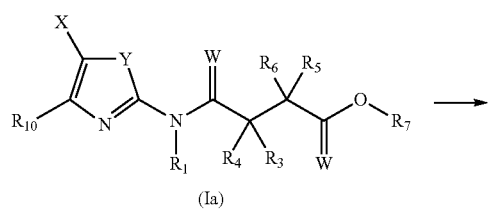

(Ia)

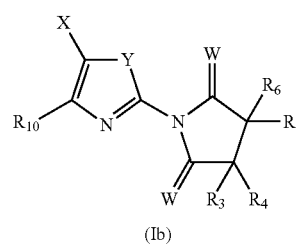

(Ib)

Alternatively, compounds of Formula (Ib) may be prepared from a compound of Formula (Ia), when $R_7$ is alkyl substituted or not such methyl by heating in presence of a acid or a base, such as hydrogen chloride or cesium carbonate and, optionally in the presence of a nucleophilic catalyst such as potassium iodide.

SCHEME 10

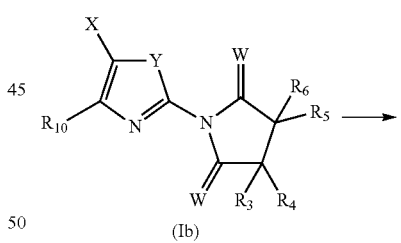

Compounds of Formula (If) wherein W is O may be prepared from a compound of Formula (Ia) wherein W are oxygen, by treatment with a thio-transfer reagent, such as Lawesson's reagent or phosphorus pentasulfide.

Compounds of Formula (If) wherein W is S may be prepared from a compound of Formula (Ia) wherein W are oxygen, by treatment with a thio-transfer reagent, such as Lawesson's reagent or phosphorus pentasulfide.

SCHEME 11

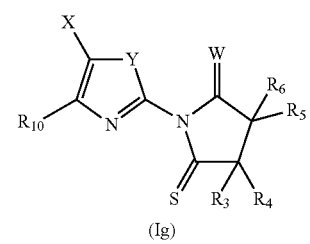

Compounds of Formula (Ig) wherein W is O may be prepared from a compound of Formula (Ib) wherein W are oxygen, by treatment with a thio-transfer reagent, such as Lawesson's reagent or phosphorus pentasulfide.

Compounds of Formula (Ig) wherein W is S may be prepared from a compound of Formula (Ib) wherein W are oxygen, by treatment with a thio-transfer reagent, such as Lawesson's reagent or phosphorus pentasulfide.

SCHEME 12

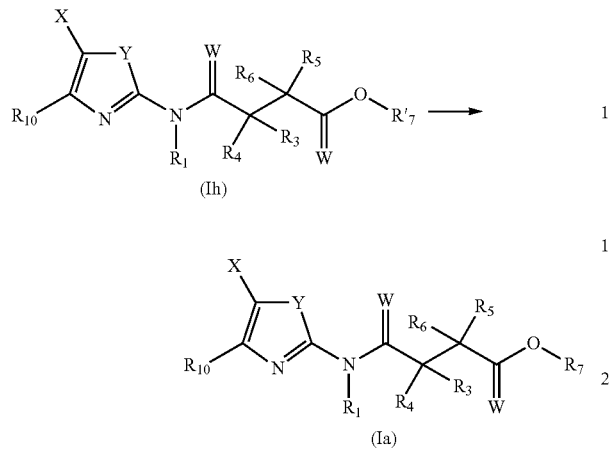

Alternatively, compounds of Formula (Ia) may be prepared from a compound of Formula (Ih) where in $R'_7$ is a alkyl derivative such as methyl via transesterification in presence of a alcohol derivative ($R_7OH$). Transesterification reactions are well known to a person skilled in the art and where reviewed, for example, in "Synthetic Organic Methodology: Comprehensive Organic Transformations. A Guide to Functional Group Preparations." Larock, R. C. 1989, p. 985-987, Publisher: (VCH, Weinheim, Fed. Rep. Ger.) or March's Advanced Organic Chemistry: Reactions, Mechanisms, and Structure, 5th Edition, Smith, Michael B.; March, Jerry. UK. 2000, Publisher: (John Wiley & Sons, Ltd., Chichester, UK) p 486-487.

Compounds of Formula (II), (III) and (IV) are either known or may be made by methods known to a person skilled in the art.

SCHEME 13

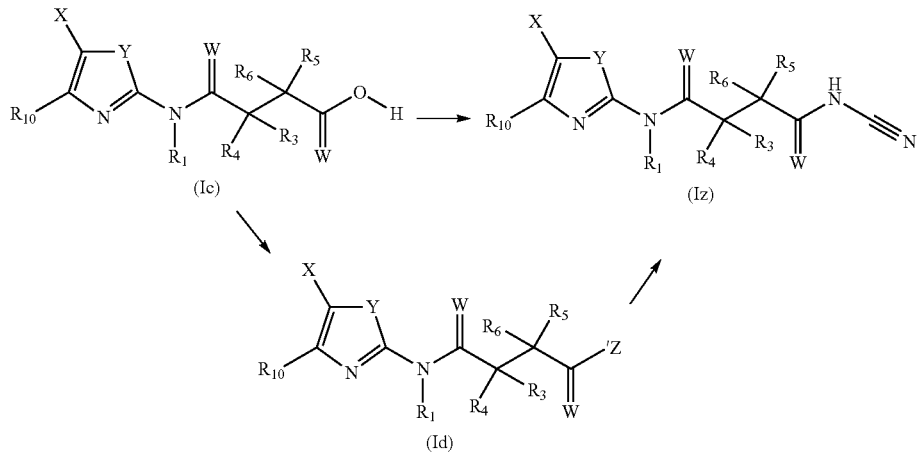

Compounds of formula (Iz) may be prepared from a compound of formula (Ic) by reaction with Cyanamide in the presence of a coupling reagent, such as DCC (N,N'-Dicyclohexylcarbodiimide), EDC (1-ethyl-3-[3-dimethyl-amino-propyl]carbodiimide hydrochloride) or BOP—Cl (bis(2-oxo-3-oxazolidinyl)phosphonic chloride), in the presence of a base, such as pyridine, triethylamine, 4-(dimethylamino)pyridine or diisopropylethylamine, and optionally in the presence of a nucleophilic catalyst, such as hydroxybenzotriazole.

Alternatively, Compounds of formula (Iz) may be prepared from a compound of formula (Id), wherein Z is a leaving group such as chlorine. The reaction may be carried out under basic conditions (for example in the presence of pyridine, triethylamine, 4-(dimethylamino)pyridine or diisopropylethylamine) and in a suitable solvent, such as, for instance, tetrahydrofuran, optionally in the presence of a nucleophilic catalyst. The reaction is carried out at a temperature of from −120° C. to +130° C., preferably from −100° C. to 100° C. Alternatively, the reaction may be conducted in a biphasic system comprising an organic solvent, preferably ethyl acetate, and an aqueous solvent, preferably a saturated solution of sodium bicarbonate.

SCHEME 14

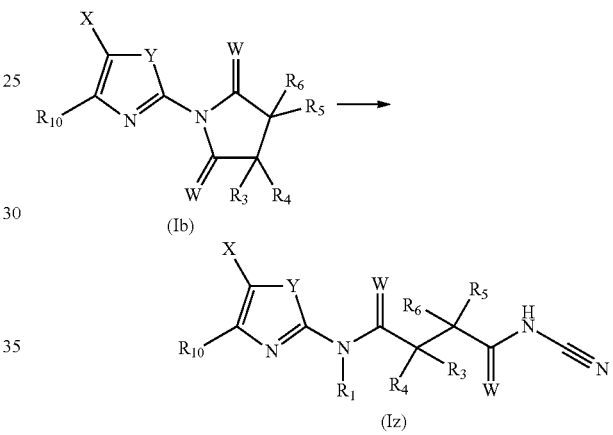

Compounds of Formula (Iz) may be prepared from a compound of Formula Ib) by reaction of amine derivatives in the presence of solvent, such as dimethylformamide or dioxane. Such reactions are usually carried out by heating or under microwave irradiation, optionally in the presence of an acid, such as acetic acid or a base, such as triethylamine or dimethylaminopyridine.

PREPARATION EXAMPLES

The following HPLC-MS methods were used for the analysis of the compounds.

Method A:

Spectra were recorded on a Mass Spectrometer from Waters (SQD or ZQ Single quadrupole mass spectrometer) equipped with an electrospray source (Polarity: positive or negative ions, Capillary: 3.00 kV, Cone range: 30-60 V, Extractor: 2.00 V, Source Temperature: 150° C., Desolvation Temperature: 350° C., Cone Gas Flow: 0 L/Hr, Desolvation Gas Flow: 650 L/Hr, Mass range: 100 to 900 Da) and an Acquity UPLC from Waters: Binary pump, heated column compartment and diode-array detector. Solvent degasser, binary pump, heated column compartment and diode-array detector. Column: Waters UPLC HSS T3, 1.8 μm, 30×2.1 mm, Temp: 60° C., DAD Wavelength range (nm): 210 to 500, Solvent Gradient: A=water+5% MeOH+0.05% HCOOH, B=Acetonitrile+0.05% HCOOH: gradient: gradient: 0 min 0% B, 100% A; 1.2-1.5 min 100% B; Flow (ml/min) 0.85

Example P1: Methyl 4-[(5-cyanothiazol-2-yl)amino]-4-oxo-butanoate (compound A1)

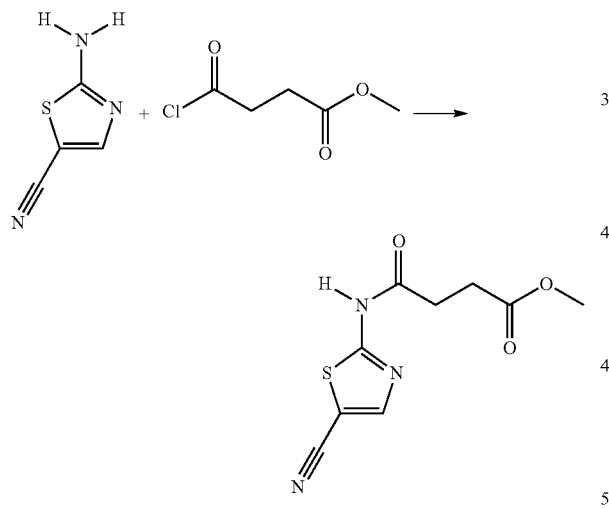

2-Aminothiazole-5-carbonitrile (1.50 g, 12.0 mmol) is dissolved in tetrahydrofuran (50 mL) with N,N-dimethylaniline (1.60 g, 13.2 mmol) then methyl 4-chloro-4-oxo-butanoate (1.98 g, 13.2 mmol) was added. The mixture was stirred for 1.5 h at room temperature. Ethyl acetate and water were added and the aqueous layer was extracted with ethyl acetate. The combined organic layers were washed with brine and dried on MgSO$_4$ and concentrated. The mixture was purified by flash chromatography eluting with dichloromethane and ethyl acetate (4/1) to give methyl 4-[(5-cyanothiazol-2-yl)amino]-4-oxo-butanoate (1.70 g, 59%). Mp=118-119° C. LCMS (Method A) RT 0.65 min, ES+ 240 (M+H$^+$).

The following compounds from table A below were prepared using a similar procedure: A2, A3, A4, A21, A22, A23, A26, A27 and A28.

Example P2: 4-[(5-cyanothiazol-2-yl)amino]-4-oxo-butanoic acid (compound A5)

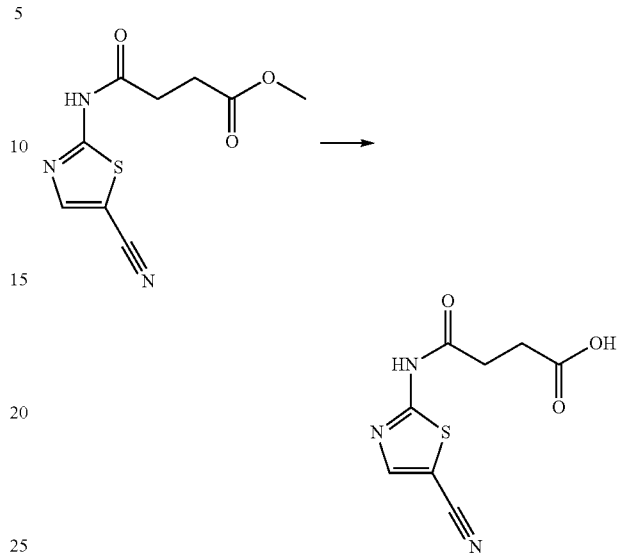

Methyl 4-oxo-4-(thiazol-2-ylamino) butanoate (compound A1) (1.70 g, 7.11 mmol) was dissolved in tetrahydrofuran (20 mL) and water (5 mL). Then lithium hydroxide monohydrate (0.596 g, 14.2 mmol) was added the solution was stirred at room temperature for 1 h. Dichloromethane and water were added and the organic layer was discarded. The aqueous phase was acidified with HCl to pH 4 and the product precipitated. The solid was filtered and dry under high vacuum to give 4-[(5-cyanothiazol-2-yl)amino]-4-oxo-butanoic acid (1.30 g, 81%);). LCMS (Method A): 0.49 min; ES+ 226 (M+H+).

The following compounds from table A below were prepared using a similar procedure: A6, A7, A8, A24 and A25.

Example 3: 2-(2,5-Dioxopyrrolidin-1-yl)thiazole-5-carbonitrile (compound B1)

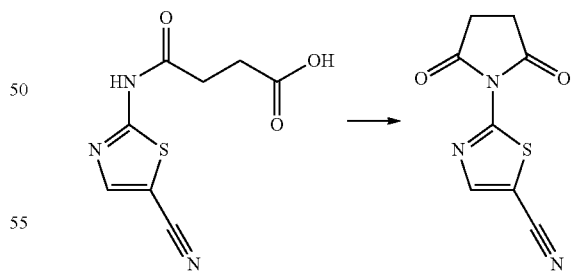

4-[(5-Cyanothiazol-2-yl)amino]-4-oxo-butanoic acid (1.25 g, 5.55 mmol) was dissolved in dichloromethane (70 mL). Oxalyl chloride (0.741 mL, 8.33 mmol) was added followed by 2 drops of N, N-dimethylformamide. The mixture was stirred at room temperature during 1 h and at 50° C. during 2 h. The solvent was removed and dry by vacuum. The residue was dissolved with ethyl acetate and washed with sat. Sodium carbonate (25 mL). The organic layers were dried on magnesium sulfate, concentrated to give 2-(2,5-dioxopyrrolidin-1-yl)thiazole-5-carbonitrile (compound B1) (0.93 g, 81%). LCMS (Method A): 1.02 min; ES+ 375 (M–H⁺).

The following compounds from table A and C were prepared using a similar procedure: B2, B3 and B4.

Example 4: (4-fluorophenyl)methyl 4-oxo-4-[[5-(trifluoromethyl)thiazol-2-yl]amino]butanoate A20

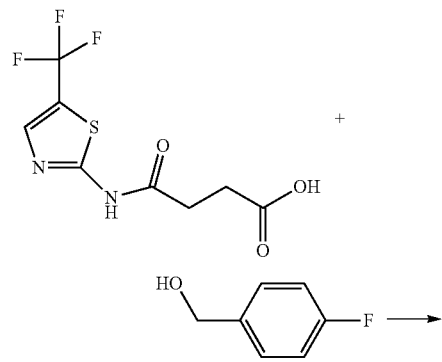

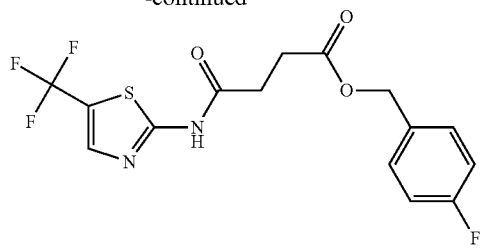

To a solution of 4-[(5-Cyanothiazol-2-yl)amino]-4-oxo-butanoic acid (250 mg, 0.932 mmol) in dichloromethane (9 mL) was added 4-fluorobenzyl alcohol (0.210 mL, 1.86 mmol), N,N-dimethylpyridin-4-amine (0.1 equiv., 11 mg) and EDCI (1.2 equiv., 0.214 g). The reaction mixture was stirred overnight and the reaction mixture was washed with HCl (1 M). The aq. phase was extracted twice with dichloromethane. The organic layers were combined, washed with NaHCO₃ (sat.), dried over Na₂SO₄ and concentrated. The residue was purified by flash chromatography to give (4-fluorophenyl)methyl 4-oxo-4-[[5-(trifluoromethyl)thiazol-2-yl]amino]butanoate (compound A20) (290 mg, 82%) as a courless solid; LCMS (Method A): 0.41 min; ES+ 208 (M+H⁺).

The following compounds from Table B were prepared using a similar procedure: A9, A10, A11, A12, A13, A14, A15, A16, A17, A18, A19, 01, 02 and C3.

TABLE A

Compounds of formula (Ia), wherein W is O, $R_3$, $R_4$, $R_5$ and $R_6$ are H (Ia)

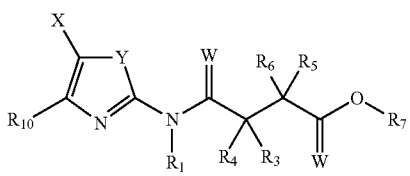

| Compound (Reference) from Table 1) | X | $R_{10}$ | Y | $R_1$ | $R_7$ | LCMS method | Retention (min.) | Mass |
|---|---|---|---|---|---|---|---|---|
| A1 (1.09) | CN | H | S | H | Me | A | 0.65 | 240 (M + H⁺) |
| A2 (1.08) | CF₃ | H | S | H | Me | A | 0.85 | 283 (M + H⁺) |
| A3 (1.06) | Cl | H | S | H | Me | A | 0.78 | 251/249 (M + H⁺) |
| A4 (1.07) | Br | H | S | H | Me | A | 0.68 | 295/293 (M + H⁺) |
| A5 (1.03) | CN | H | S | H | H | A | 0.49 | 226 (M + H⁺) |
| A6 (1.02) | CF₃ | H | S | H | H | A | 0.73 | 268 (M + H⁺) |
| A7 (1.00) | Cl | H | S | H | H | A | 0.66 | 237/235 (M + H⁺) |
| A8 (1.01) | Br | H | S | H | H | | | 1H (400 MHz, DMSO-d6) ☐12.35 (1 H, brs), 12.25 (1 H, brs), 7.52 (1 H, s), 2.68 (2 H, t), 2.52 (2 H, t) |
| A9 | Br | H | S | H | CH₂CF₃ | A | 0.93 | 361/363 (M + H⁺) |
| A10 | Br | H | S | H | CH₂CCH | A | 0.85 | 319/317 (M + H⁺) |
| A11 | Br | H | S | H | CH₂CH₂OMe | A | 0.79 | 261/259 (M + Na⁺) |
| A12 | Br | H | S | H | CH₂(4-F)Ph | A | 0.99 | 387/385 (M – H⁺) |
| A13 | CN | H | S | H | CH₂CF₃ | A | 0.83 | 306 (M – H⁺) |
| A14 | CN | H | S | H | CH₂CCH | A | 0.72 | 262 (M – H⁺) |
| A15 | CN | H | S | H | CH₂CH₂OMe | A | 0.68 | 282 (M – H⁺) |
| A16 | CN | H | S | H | CH₂(4-F)Ph | A | 0.90 | 332 (M – H⁺) |
| A17 | CF₃ | H | S | H | CH₂CF₃ | A | 0.97 | 351 (M + H⁺) |
| A18 | CF₃ | H | S | H | CH₂CCH | A | 0.89 | 305 (M – H⁺) |
| A19 | CF₃ | H | S | H | CH₂CH₂OMe | A | 0.86 | 327 (M + H⁺) |
| A20 | CF₃ | H | S | H | CH₂(4-F)Ph | A | 1.02 | 375 (M – H⁺) |
| A21 | CN | OMe | S | H | Me | A | 0.75 | 268 (M + H⁺) |
| A22 | Me | H | S | H | Me | A | 0.67 | 229 (M + H⁺) |
| A23 | CO₂Me | H | S | H | Me | A | 0.71 | 273 (M + H⁺) |
| A24 | CN | OMe | S | H | H | A | 0.65 | 254 (M – H⁺) |
| A25 | Me | H | S | H | H | A | 0.52 | 213 (M + H⁺) |
| A26 | CHF₂ | H | S | H | Me | A | 0.73 | 265 (M + H⁺) |

TABLE A-continued

Compounds of formula (Ia), wherein W is O, $R_3$, $R_4$, $R_5$ and $R_6$ are H

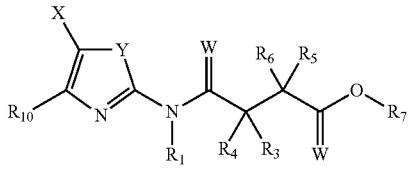

(Ia)

| Compound (Reference) from Table 1) | X | $R_{10}$ | Y | $R_1$ | $R_7$ | Physical data | | |
|---|---|---|---|---|---|---|---|---|
| | | | | | | LCMS method | Retention (min.) | Mass |
| A27 | OMe | H | S | H | Me | A | 0.65 | 245 (M + H$^+$) |
| A28 | SMe | H | S | H | Me | A | 0.77 | 261 (M + H$^+$) |
| A29 | SMe | H | S | H | H | A | 0.65 | 247 (M + H$^+$) |

TABLE B

Compounds of formula (Ib), wherein W is O, $R_3$, $R_4$, $R_5$ and $R_6$ are H

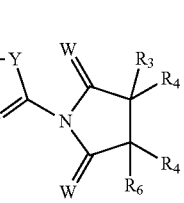

(Ib)

| Compound (Reference from Table 2) | X | Y | $R_{10}$ | Physical data | | |
|---|---|---|---|---|---|---|
| | | | | LCMS Method | Retention (min.) | Mass |
| B1 (2.04) | CN | S | H | A | 0.41 | 208 (M + H$^+$) |
| B2 (2.03) | CF$_3$ | S | H | A | 0.75 | 251 (M + H$^+$) |
| B3 (2.00) | Cl | S | H | A | 0.62 | 219/217 (M + H$^+$) |
| B4 (2.01) | Br | S | H | A | 0.65 | 263/261 (M + H$^+$) |

TABLE C

Compounds of formula (Ib), wherein W is O, $R_3$, $R_4$, $R_5$ and $R_6$ are H

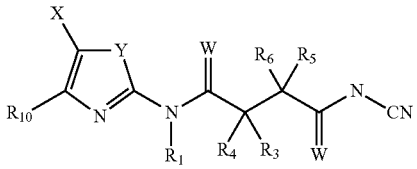

(Iz)

| Compound (Reference from Table 3) | X | $R_{10}$ | Y | $R_1$ | Physical data | | |
|---|---|---|---|---|---|---|---|
| | | | | | LCMS Method | Retention (min.) | Mass |
| C1 (3.03) | CN | H | S | H | A | 0.47 | 250 (M + H$^+$) |
| C2 (3.02) | CF$_3$ | H | S | H | A | 0.75 | 293 (M + H$^+$) |
| C3 (3.01) | Br | H | S | H | A | 0.67 | 305/303 (M + H$^+$) |

BIOLOGICAL EXAMPLES

Two bioassays were developed in order to assay the activity of the compounds of the present invention. In the first assay, the activity of the compound was quantified in beans based on its effect on the elongation of the petiole of the second leaf. In the second assay, the compound's effect on the root growth of wheat was determined.

Example B1 Bean Assay

French beans (*Phaseolus vulgaris*) of the variety Fulvio were sown in 0.5 L pots in a sandy loam without additional fertilizer. Plants grew under greenhouse conditions at 22/18° C. (day/night) and 80% relative humility; light was supplemented above 25 kLux. Plants were treated with test compounds eleven days after sowing, when the second internode was 2-5 mm long. Before application, the compounds were each dissolved in dimethyl sulfoxide and diluted in a mixture of ethanol and water (1:1 ratio by volume). Five micro liters of the test compound was pipetted to the wound created after abscising the bract leaf from the base of the second internode. Fourteen days after application, the length of the petiole of the second leaf (measured from the base of the petiole to the base of the first leaflet) was determined in order to quantify the activity of the compounds.

The following compounds gave at least an increase of 10% of the length of the petiole of the second leaf: A5, B1, A2, A6, B2, A13, A14, A17, A18, C1, C2.

Example B2 Wheat Assay

The test compounds were dissolved in small volumes of dimethyl sulfoxide and diluted to the appropriate concentration with water. Wheat (*Triticum aestivum*) seeds of the variety Arina were sown in pouches (14.7×13.2 cm) containing 10 mL of the appropriate compound solution. The pouches were stored at 17° C. for three days to enable the seeds to germinate. Plants were then stored at 5° C. Twelve days after sowing/application, plants were removed from the pouches and scanned. The effect of the compounds was quantified by determining plant (root and shoot) area and curliness of the roots (curliness is an indicator of brassinosteroid-type activity).

The following compounds gave at least a reduction of 5% of the plant (root and shoot) area and showed a curly root phenotype: A3, B2, A6, A2, A5, A1, B4, A8.

Example B3 In Vitro Assay to Test for Inhibition of Plant GSK3/Shaggy-Like Kinase Activity

*Arabidopsis* BIN2 kinase (Uniprot Q39011) was produced in *E. coli* BL21 as an N-terminal hexahistidine fusion protein. In vitro kinase assays were performed by incubating 50 ng $His_6$-BIN2 protein with 5 µg myelin basic protein (Sigma-Aldrich) as substrate and 5 µM ATP as co-substrate in reaction buffer consisting of 40 mM Tris-HCl, 20 mM $MgCl_2$ and 0.1 mg/mL bovine serum albumin in a final reaction volume of 50 µl. Enzyme activity was assessed in the absence and presence of compounds (described in Tables A and B) at 5 µM by measuring the level of ADP produced after incubation for 1 h at 20° C. using an enzyme-coupled bioluminescent assay (ADP-Glo, Promega Corp.). The experiment was performed in triplicate and principaly on the acid form (as it the active A1).

The following compounds inhibited the activity of $His_6$-BIN2 by at least 20% relative to the solvent vehicle control: A5, A6, A7, A8.

The invention claimed is:

1. A plant growth regulator or seed germination promoting composition, comprising:
an agrochemically effective amount of a compound according to formula (I):

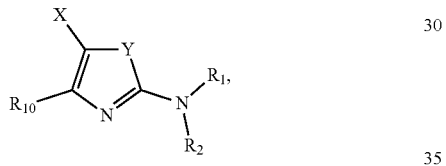

wherein:
Y is O or S;
$R_{10}$ is H, halogen, $C_1$-$C_6$ alkyl, $C_1$-$C_6$ alkoxy, $C_1$-$C_6$ haloalkyl or cyano;
X is halogen, $C_1$-$C_6$ haloalkyl, thiocyanate, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, $C_2$-$C_6$ alkenyl, $C_2$-$C_6$ alkynyl, amine, N—$C_1$-$C_6$ alkyl amine, N,N-di-$C_1$-$C_6$ alkyl amine, $C_1$-$C_6$ alkylcarbonyl, $C_1$-$C_6$ alkoxycarbonyl, $C_1$-$C_6$ haloalkoxycarbonyl, $C_1$-$C_6$ haloalkylcarbonyl, $C_3$-$C_8$ cycloalkyl, formyl or mercapto;
$R_1$ is H, $C_1$-$C_6$ alkyl, $C_1$-$C_6$ haloalkyl, $C_1$-$C_6$ alkylcarbonyl, $C_1$-$C_6$ alkoxycarbonyl; or
$R_1$ is $C_1$-$C_6$ alkyl substituted by one or more cyano, amine, carbonylamine;
$R_2$ is a group according to formula (I'):

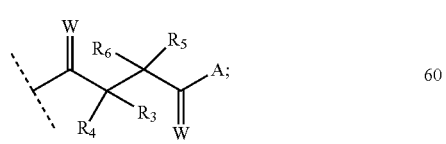

or
$R_1$ and $R_2$ form a cyclic group around the nitrogen according to formula (I"):

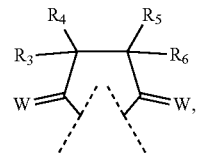

wherein:
each W is independently O or S;
A is —$OR_7$ or —NHCN;
$R_3$, $R_4$, $R_5$ and $R_6$ are each independently hydrogen, halogen, nitro, cyano, $C_1$-$C_3$ alkyl, $C_1$-$C_3$ haloalkyl, $C_1$-$C_3$ alkoxy, hydroxyl, —OC(O)$R_8$, amine, N—$C_1$-$C_3$ alkyl amine or N,N-di-$C_1$-$C_3$ alkyl amine; wherein $R_8$ is hydrogen, $C_1$-$C_6$ alkyl, $C_1$-$C_6$ alkoxy, or $C_1$-$C_6$ haloalkyl;
$R_7$ is hydrogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_7$ cycloalkyl, aryl or aryl substituted by one to five substituents $R_9$, heterocyclyl or heterocyclyl substituted by one to five substituents $R_9$; or
$R_7$ is $C_1$-$C_6$ alkyl substituted by one or more cyano, nitro, amine, hydroxyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkyl-sulfonyl, $C_3$-$C_7$ cycloalkyl, N—$C_1$-$C_6$ alkyl amine, N,N-di-$C_1$-$C_6$ alkyl amine, aryl or aryl substituted by one to five substituents $R_9$, heterocyclyl or heterocyclyl substituted by one to five substituents $R_9$;
each $R_9$ is independently cyano, nitro, amino, hydroxyl, halogen, $C_1$-$C_6$ alkyl, $C_1$-$C_6$ haloalkyl, $C_2$-$C_6$ alkenyl, $C_2$-$C_6$ haloalkenyl, $C_2$-$C_6$ alkynyl, $C_2$-$C_6$ haloalkynyl, $C_3$-$C_6$ cycloalkyl, $C_3$-$C_6$ halocycloalkyl, $C_1$-$C_6$ alkoxy, $C_1$-$C_6$ haloalkoxy, $C_1$-$C_6$ alkylthio, $C_1$-$C_6$ haloalkylthio, $C_1$-$C_6$ alkylsulfinyl, $C_1$-$C_6$ haloalkylsulfinyl, $C_1$-$C_6$ alkylsulfonyl, $C_1$-$C_6$ haloalkylsulfonyl, N—$C_1$-$C_6$ alkylamino, N,N-di-($C_1$-$C_6$ alkyl)-amino, N,N-di-($C_1$-$C_6$ alkyl)aminocarbonyl, N,N-di-($C_1$-$C_6$ alkyl) aminosulfonyl, $C_1$-$C_6$ alkylcarbonyl, $C_1$-$C_6$ alkylcarbonyloxy, $C_1$-$C_6$ alkoxycarbonyl, $C_1$-$C_6$ alkyl-carbonylamino;
and any salts or N-oxides thereof;
excluding the following compounds (i) to (viii):

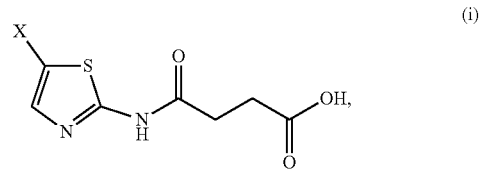

wherein X is $NO_2$, HCO or Br;

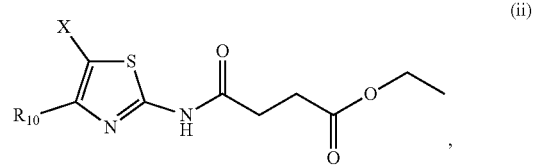

wherein X is CN or Br and R$_{10}$ is H; or wherein X is CN and R$_{10}$ is CF$_3$;

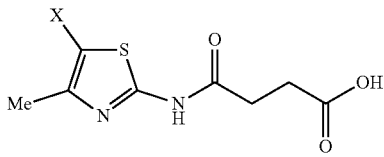
(iii)

wherein X is Br, I, COCH$_2$Br, C(O)Me, COOMe, COOEt, COO$^i$Pr or COO$^i$Bu;

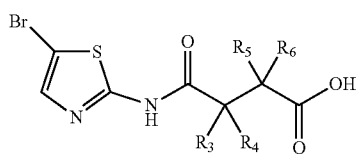
(iv)

wherein R$^3$ is H, R$^4$ is NH$_2$ and R$_5$ and R$_6$ are H; or wherein R$_3$ and R$_4$ are H, and R$_5$ and R$_6$ are ethyl; or wherein R$_3$ and R$_4$ are H, R$_5$ is methyl and R$_6$ is $^i$Pr;

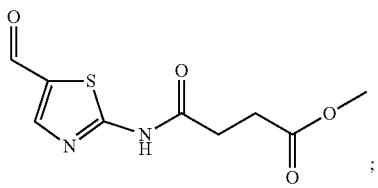
(v)

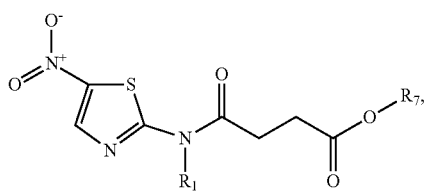
(vi)

wherein R$_1$ is CH$_2$CH$_2$CONH$_2$ or CH$_2$CH$_2$CN and R$_7$ is methyl or ethyl;

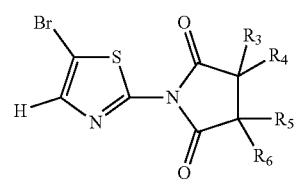
(vii)

wherein R$_3$, R$_4$, R$_5$, and R$_6$ are H; or wherein R$_3$, and R$_4$ are H and R$_5$, R$_6$ are ethyl; or wherein R$_3$, and R$_4$ are H, R$_5$ is methyl and R$_6$ is $^i$Pr; or wherein R$_3$ is methyl and R$_4$, R$_5$, and R$_6$ are H; and

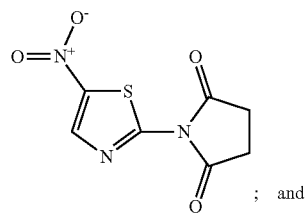
(viii)
; and an agriculturally acceptable formulation adjuvant.

2. The composition according to claim 1 comprising the compound of Formula I, wherein:
R$_2$ is the group according to formula (I');
A is —OR$_7$;
Y is S;
each W is O;
R$_1$ is H or C$_1$-C$_6$ alkyl;
X is halogen, or trifluoromethyl;
R$_3$, R$_4$, R$_5$ and R$_6$ are each independently hydrogen, halogen, nitro, cyano, C$_1$-C$_3$ alkyl, C$_1$-C$_3$ haloalkyl, C$_1$-C$_3$ alkoxy, or hydroxyl;
R$_7$ is hydrogen, C$_1$-C$_6$ alkyl, C$_1$-C$_6$ haloalkyl, C$_2$-C$_6$ alkenyl, C$_2$-C$_6$ alkynyl, or R$_7$ is C$_1$-C$_6$ alkyl substituted by C$_1$-C$_6$ alkoxy, C$_1$-C$_6$ alkylthio or aryl; and
R$_{10}$ is hydrogen, halogen, C$_1$-C$_6$ haloalkyl or cyano.

3. The composition according to claim 1 comprising the compound of Formula I, wherein:
R$_2$ is the group according to formula (I');
A is —OR$_7$;
Y is S;
each W is O;
R$_1$ is H or C$_1$-C$_6$ alkyl;
X is CO$_2$Me, CHF$_2$, OMe, SMe;
R$_3$, R$_4$, R$_5$ and R$_6$ are each independently hydrogen, halogen, nitro, cyano, C$_1$-C$_3$ alkyl, C$_1$-C$_3$ haloalkyl, C$_1$-C$_3$ alkoxy, or hydroxyl;
R$_7$ is hydrogen, C$_1$-C$_6$ alkyl, C$_1$-C$_6$ haloalkyl, C$_2$-C$_6$ alkenyl, C$_2$-C$_6$ alkynyl, or R$_7$ is C$_1$-C$_6$ alkyl substituted by C$_1$-C$_6$ alkoxy, C$_1$-C$_6$ alkylthio or aryl; and
R$_{10}$ is hydrogen, halogen, C$_1$-C$_6$ haloalkyl or cyano.

4. The composition according to claim 1 comprising the compound of Formula I, wherein:
R$_2$ is the group according to formula (I');
A is —NHCN;
Y is S;
each W is O;
R$_1$ is H or C$_1$-C$_6$ alkyl;
X is halogen, or trifluoromethyl;
R$_3$, R$_4$, R$_5$ and R$_6$ are each independently hydrogen, halogen, nitro, cyano, C$_1$-C$_3$ alkyl, C$_1$-C$_3$ haloalkyl, C$_1$-C$_3$ alkoxy, or hydroxyl; and
R$_{10}$ is hydrogen, halogen, C$_1$-C$_6$ haloalkyl or cyano.

5. The composition according to claim 1 comprising the compound of Formula I, wherein R$_1$ is hydrogen, methyl, ethyl or propyl.

6. The composition according to claim 1 comprising the compound of Formula I, wherein R$_7$ is hydrogen, methyl, ethyl or benzyl.

7. The composition according to claim 1 comprising the compound of Formula I, wherein:
R$_1$ and R$_2$ form a cyclic group around the nitrogen according to formula (I'');
Y is S;
each W is O;

X is halogen, or trifluoromethyl;

$R_3$, $R_4$, $R_5$ and $R_6$ are each independently hydrogen, halogen, nitro, cyano, $C_1$-$C_3$ alkyl, $C_1$-$C_3$ haloalkyl, $C_1$-$C_3$ alkoxy, or hydroxyl;

$R_{10}$ is hydrogen, halogen, $C_1$-$C_6$ haloalkyl or cyano.

8. The composition according to claim 1 comprising the compound of Formula I, wherein X is bromine, chlorine, or trifluoromethyl.

9. The composition according to claim 1 comprising the compound of Formula I, wherein $R_3$, $R_4$, $R_5$ and $R_6$ are each independently hydrogen or $C_1$-$C_3$ alkyl.

10. The composition according to claim 1 comprising the compound of Formula I, wherein $R_{10}$ is hydrogen, chlorine, bromine, trifluoromethyl or cyano.

11. The composition according to claim 9 comprising the compound of Formula I, wherein $R_3$, $R_4$, $R_5$ and $R_6$ are each independently hydrogen, methyl, ethyl, or iso-propyl.

12. The composition according to claim 11 comprising the compound of Formula I, wherein $R_3$, $R_4$, $R_5$ and $R_6$ are each hydrogen.

13. The composition according to claim 10 comprising the compound of Formula I, wherein $R_{10}$ is hydrogen.

14. The composition of claim 1, wherein the agrochemically effective amount of a compound of formula (I) is effective as a plant growth regulator.

15. The composition of claim 1, wherein the agrochemically effective amount of a compound of formula (I) is effective as a seed germination promoter.

16. The composition of claim 1, wherein the agriculturally acceptable formulation adjuvant is present in an agrochemically effective amount.

* * * * *